United States Patent
Yang et al.

(10) Patent No.: US 10,307,442 B2
(45) Date of Patent: Jun. 4, 2019

(54) PHARMACEUTICAL COMPOSITION FOR THE PREVENTION OR TREATMENT OF A PULMONARY DISORDER COMPRISING MESENCHYMAL STEM CELLS HAVING IMPROVED PROLIFERATION AND DIFFERENTIATION CAPACITY

(71) Applicant: MEDIPOST CO., LTD., Seongnam-si, Gyeonggi-do (KR)

(72) Inventors: Yoon Sun Yang, Seongnam-si (KR); Wonil Oh, Seongnam-si (KR); Hye Jin Jin, Seongnam-si (KR); Hong Bae Jeon, Seongnam-si (KR); Miyeon Kim, Seongnam-si (KR)

(73) Assignee: MEDIPOST CO., LTD., Seongnam-si (KR)

( * ) Notice: Subject to any disclaimer, the term of this patent is extended or adjusted under 35 U.S.C. 154(b) by 0 days.

(21) Appl. No.: 15/540,334

(22) PCT Filed: Mar. 4, 2016

(86) PCT No.: PCT/KR2016/002203
§ 371 (c)(1),
(2) Date: Jun. 28, 2017

(87) PCT Pub. No.: WO2016/140547
PCT Pub. Date: Sep. 9, 2016

(65) Prior Publication Data
US 2017/0360839 A1    Dec. 21, 2017

(30) Foreign Application Priority Data
Mar. 4, 2015 (KR) ......................... 10-2015-0030568

(51) Int. Cl.
*A61K 35/28* (2015.01)
*C12N 5/073* (2010.01)
*C12N 5/0775* (2010.01)

(52) U.S. Cl.
CPC ............ *A61K 35/28* (2013.01); *C12N 5/0605* (2013.01); *C12N 5/0663* (2013.01); *C12N 5/0667* (2013.01); *C12N 5/0668* (2013.01)

(58) Field of Classification Search
CPC .... A61K 35/28; C12N 5/0605; C12N 5/0663; C12N 5/0667; C12N 5/0668
USPC ........................................................ 424/489
See application file for complete search history.

(56) References Cited

U.S. PATENT DOCUMENTS

2009/0274665 A1* 11/2009 Akabutu ................ A61K 35/28
424/93.7

FOREIGN PATENT DOCUMENTS

| JP | 2014-073084 A | 4/2014 |
| JP | 2014-131507 A | 7/2014 |
| WO | 2007/124594 A1 | 11/2007 |

OTHER PUBLICATIONS

Zhidkova et al., Preparation and Characteristics of Growth and Marker Properties of Urinary Bladder Mesenchymal Stem Cells, Journal of Evolutionary Biochemistry and Physiology, 2013, vol. 49, No. 1, pp. 105.-116.*
Qin et al., Amphiregulin Is a Novel Growth Factor Involved in Normal Bone Development and in the Cellular Response to Parathyroid Hormone Stimulation, The Journal of Biological Chemistry, 2005, vol. 280, No. 5, Issue of Feb. 4, pp. 3974-3981.*
Gabrielis Kundrotas, "Surface markers distinguishing mesenchymal stem cells from fibroblasts", Acta Medica Lituanica, 2012, pp. 75-79, vol. 19, No. 2.
Georg Hansmann et al., "Mesenchymal stem cell-mediated reversal of bronchopulmonary dysplasia and associated pulmonary hypertension", Pulmonary Circulation, Apr.-Jun. 2012, pp. 170-181, vol. 2, No. 2.
International Searching Authority, International Search Report of PCT/KR2016/002203 dated Aug. 22, 2016 [PCT/ISA/210].
International Searching Authority, Written Opinion of PCT/KR2016/002203 dated Aug. 22, 2016 [PCT/ISA/237].

* cited by examiner

Primary Examiner — Jennifer M. H. Tichy
(74) Attorney, Agent, or Firm — Sughrue Mion, PLLC

(57) ABSTRACT

A pharmaceutical composition for the prevention or treatment of a pulmonary disorder is provided. The composition contains mesenchymal stem cells showing improved proliferation and differentiation capacity which are characterized by the expression or non-expression of one or more particular cell markers. Also, provided is a method for obtaining mesenchymal stem cells showing improved proliferation and differentiation capacity based on the expression or non-expression of such cell markers. The mesenchymal stem cells having improved proliferation and differentiation capacity can be easily obtained from mesenchymal stem cells of various origins based on the expression or non-expression of CD26, CD49f, CD146 and EGFR. The mesenchymal stem cells thus obtained can be effectively used for the prevention or treatment of a pulmonary disorder such as, for example, pulmonary emphysema.

15 Claims, 33 Drawing Sheets
(3 of 33 Drawing Sheet(s) Filed in Color)
Specification includes a Sequence Listing.

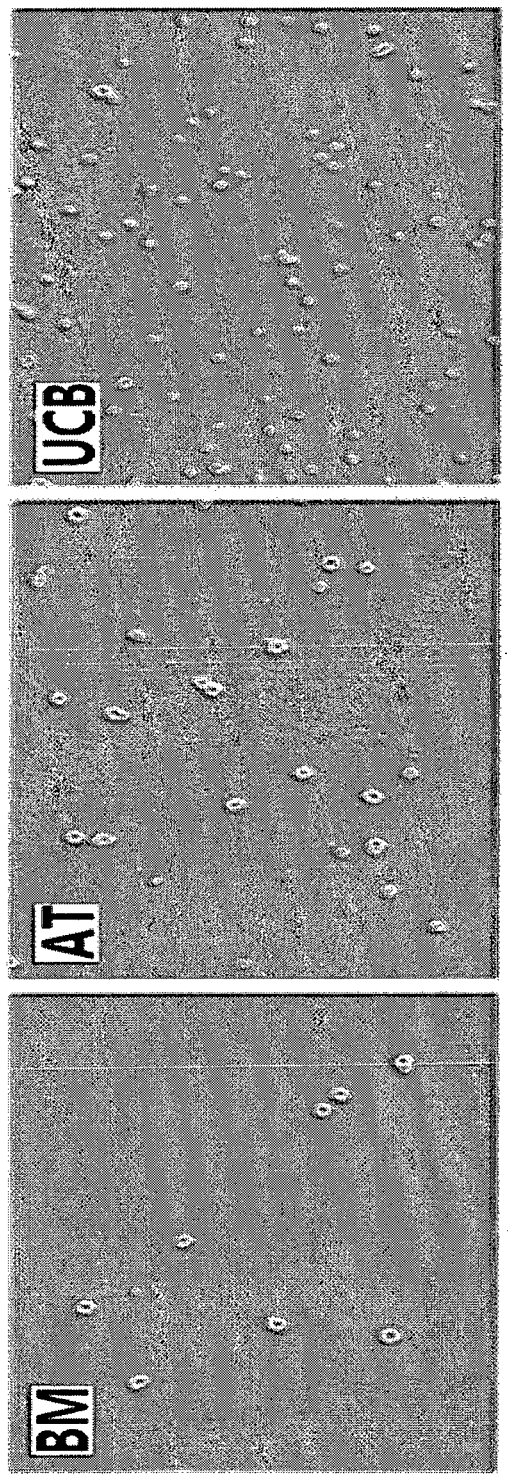

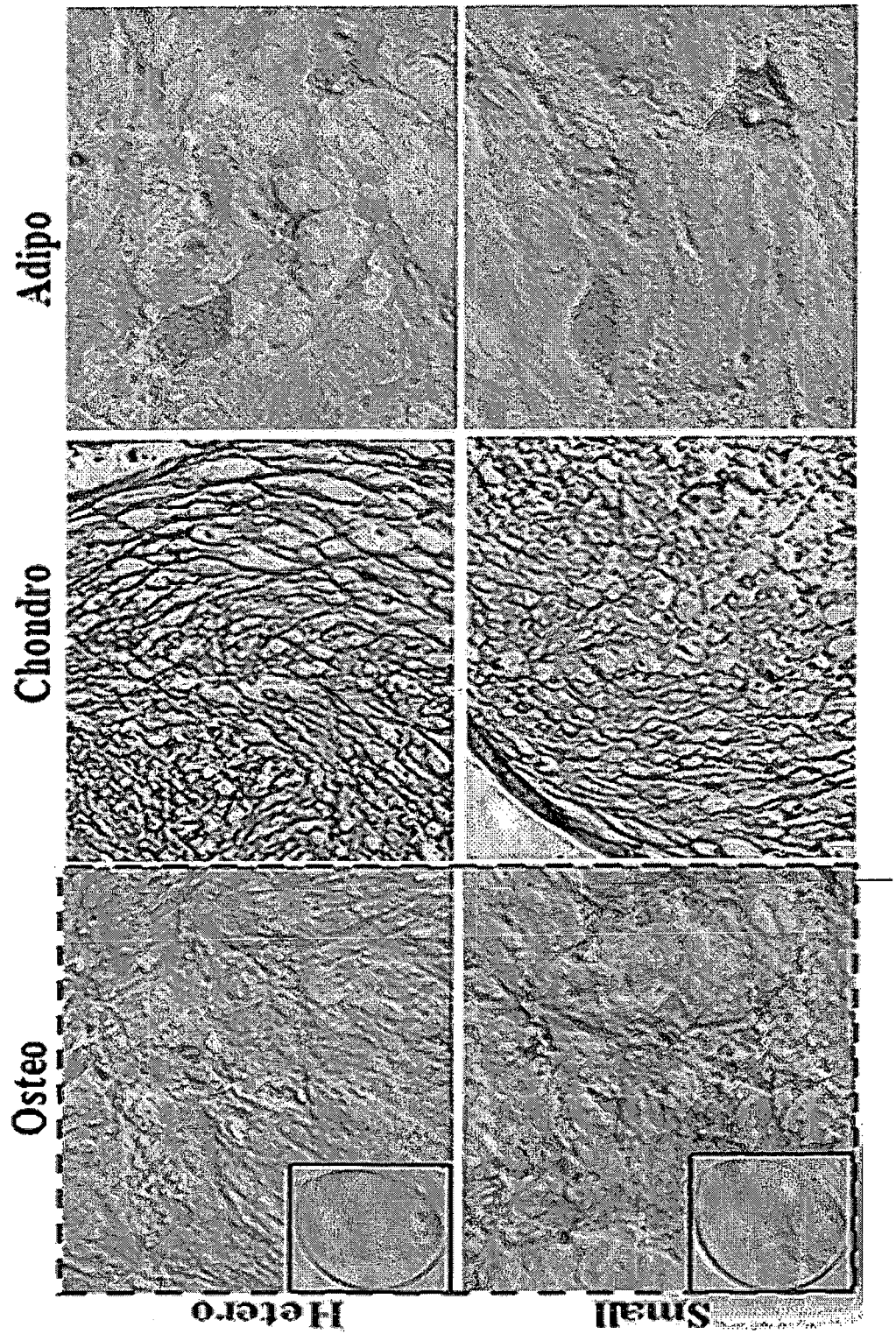

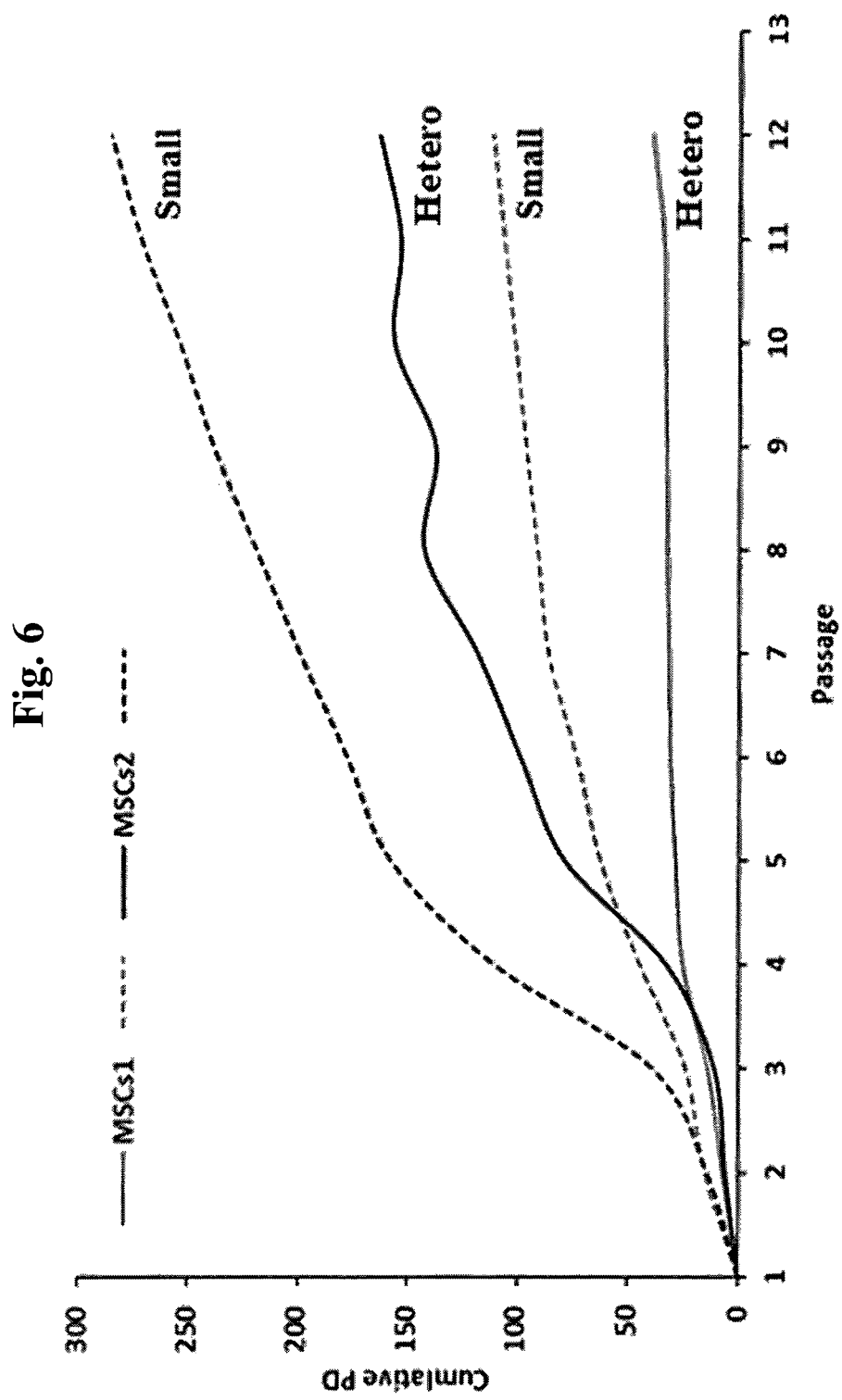

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Oct4 forward primer

<400> SEQUENCE: 1
caatttgcca agctcctga                                                 19

<210> SEQ ID NO 2
<211> LENGTH: 20
<212> TYPE: DNA
<213> ORGANISM: Artificial Sequence
<220> FEATURE:
<223> OTHER INFORMATION: Oct4 reverse primer

<400> SEQUENCE: 2
cgtttggctg aataccttcc                                                20

<210> SEQ ID NO 3
<211> LENGTH: 20
<212> TYPE: DNA
<213> ORGANISM: Artificial Sequence
<220> FEATURE:
<223> OTHER INFORMATION: Nanog forward primer

<400> SEQUENCE: 3
agatgcctca cacggagact                                                20

<210> SEQ ID NO 4
<211> LENGTH: 20
<212> TYPE: DNA
<213> ORGANISM: Artificial Sequence
<220> FEATURE:
<223> OTHER INFORMATION: Nanog reverse primer

<400> SEQUENCE: 4
tttgcgacac tcttctctgc                                                20

<210> SEQ ID NO 5
<211> LENGTH: 20
<212> TYPE: DNA
<213> ORGANISM: Artificial Sequence
<220> FEATURE:
<223> OTHER INFORMATION: GADPH forward primer

<400> SEQUENCE: 5
agccaccatc gctcagacac                                                20

<210> SEQ ID NO 6
<211> LENGTH: 19
<212> TYPE: DNA
<213> ORGANISM: Artificial Sequence
<220> FEATURE:
```

```
<223> OTHER INFORMATION: GADPH reverse primer

<400> SEQUENCE: 6
gcccaatacg accaaatcc                                                    19
```

PHARMACEUTICAL COMPOSITION FOR THE PREVENTION OR TREATMENT OF A PULMONARY DISORDER COMPRISING MESENCHYMAL STEM CELLS HAVING IMPROVED PROLIFERATION AND DIFFERENTIATION CAPACITY

CROSS REFERENCE TO RELATED APPLICATIONS

This application is a National Stage of International Application No. PCT/KR2016/002203, filed Mar. 4, 2016, claiming priority based on Korean Patent Application No. 10-2015-0030568, filed Mar. 4, 2015, the contents of all of which are incorporated herein by reference in their entirety.

TECHNICAL FIELD

The present invention relates to a pharmaceutical composition comprising mesenchymal stem cells having improved proliferation and differentiation capacity. More particularly, the present invention relates to a pharmaceutical composition for the prevention or treatment of a pulmonary disorder comprising mesenchymal stem cells having improved proliferation and differentiation capacity which are characterized by is the expression or non-expression of one or more particular cell markers. Also, the present invention relates to a method for obtaining mesenchymal stem cells having improved proliferation and differentiation capacity based on the expression or non-expression of such cell markers.

BACKGROUND ART

A "stem cell" is a generic name for an undifferentiated type of body cell found in tissues of embryos, fetuses and adults, which has the potential of differentiating into a diverse range of specialized cell types.

Mesenchymal stem cells are multipotent stem cells that can differentiate into a variety of cell types, including adipocytes, osteoblasts, chondrocytes, myoblasts, neuroblasts, myocardioblasts, hepatocytes, islet beta cells, vascular cells, etc., and are known to have the function of modulating self-regeneration, cell migration, and immune responses. Based on these excellent properties, mesenchymal stem cells have been developed as a cell therapeutic agent.

Mesenchymal stem cells may be isolated from various tissues such as bone marrow, umbilical cord blood, adipose tissue, etc. However, when mesenchymal stem cells are used as an exogenous cell therapeutic agent, a limited pool of mesenchymal stem cells does not allow other available options, even in the case of low in vivo activity.

In addition, in order to apply the mesenchymal stem cells to clinical practice, it is essential to obtain a large amount of cells in initial stages and to culture them with passages, due to limited quantity of mesenchymal stem cells which can be obtained from tissues. However, mesenchymal stem cells form a very heterogeneous group during passages, which affects proliferation, differentiation, and senescence of the cells, rendering the mesenchymal stem cells difficult to be developed as therapeutic agents.

As such, in order to obtain a more homogeneous cell population having improved proliferation and differentiation capacity, there is a need to discover cell marker which can represent such a cell population.

For instance, Majore I. et al. disclose cell markers such as CD44, CD73, CD90, is and CD105 for identifying a subpopulation in mesenchymal stem cell-like cultures from human umbilical cord (*Cell Column. Signal.*, 2009, Mar. 20;7:6). In addition, the International Society for Cellular therapy proposed cell markers such as CD19, CD34, CD45, CD73, CD90, CD105, CD166, HLA-ABC and HLA-DR. However, the above-mentioned conventional cell markers are also expressed in a heterogeneous cell population and similar expressions can also be found in fibroblast. Accordingly, such cell markers are unsuitable as cell markers which can represent a more homogeneous cell population having improved proliferation and differentiation capacity.

Thus, the present inventors have endeavored to develop mesenchymal stem cells which are useful as a cell therapeutic agent, and found that CD26, CD49f, CD146 or EGFR is a cell marker which can represent a cell population having improved proliferation and differentiation capacity.

DISCLOSURE OF INVENTION

Technical Problem

An object of the present invention is to provide a pharmaceutical composition for the prevention or treatment of a pulmonary disorder comprising mesenchymal stem cells having improved proliferation and differentiation capacity.

Another object of the present invention is to provide a method for obtaining mesenchymal stem cells having improved proliferation and differentiation capacity, based on the expression or non-expression of one or more particular cell markers.

Solution to Problem

The present invention provides a pharmaceutical composition for the prevention or treatment of a pulmonary disorder comprising mesenchymal stem cells as an active ingredient, wherein the mesenchymal stem cells do not express CD26.

The present invention also provides a method for obtaining mesenchymal stem cells having improved proliferation and differentiation capacity, comprising separating mesenchymal stem cells which do not express CD26 as a cell marker from unseparated mesenchymal stem cells.

Advantageous Effects of Invention

According to a method of the present invention, the mesenchymal stem cells having improved proliferation and differentiation capacity can be easily obtained from the mesenchymal stem cells of various origins based on the expression or non-expression of a particular cell marker such as CD26. The mesenchymal stem cells thus obtained can be effectively used for the prevention or treatment of a pulmonary disorder such as, for example, pulmonary emphysema.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A to 1C are photographs and a graph of bone marrow-derived mesenchymal stem cells (BM), adipose tissue-derived mesenchymal stem cells (AT) and umbilical cord blood-derived mesenchymal stem cells (UCB). FIG. 1A shows the mesenchymal stem cells in the adherent form before trypsin treatment, FIG. 1B shows those in the form of single cells after trypsin treatment, and FIG. 1C shows the result of size distribution analyzed by Cellometer.

FIG. 5 provides photographs showing the osteogenic (Osteo), chondrogenic (Chondro) and adipogenic (Adipo) differentiations before and after size separation.

FIG. 6 shows CPD of mesenchymal stem cells (MSCs1 & MSCs2) obtained from 2 donors before and after size separation which were each cultured with passages.

FIG. 26 also provides a graph showing the mean linear intercept(MLI) in each cell group.

MODE FOR CARRYING OUT INVENTION

Figure 1A:
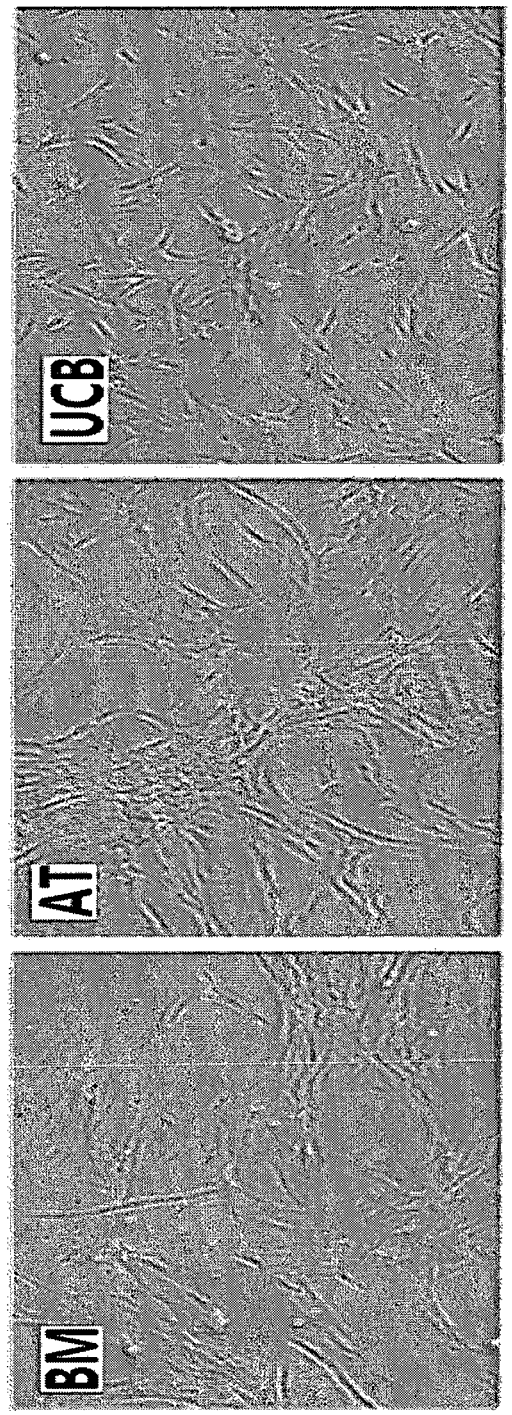

The present invention provides a pharmaceutical composition for the prevention or treatment of a pulmonary disorder comprising mesenchymal stem cells as an active ingredient, wherein the mesenchymal stem cells do not express cluster of differentiation 26(CD26) as a cell marker.

CD26, a dipeptidyl peptidase-4 (DPP4), which is also known as adenosine deaminase protein complex 2, is a protein encoded by the DPP4 gene in humans. This protein is an antigenic enzyme expressed on the surface of most kinds of cells, which is related with immune regulation, signal transduction and apoptosis. In addition, this protein is known to act as an inhibitor of the development of cancer and tumor. However, its relationship with proliferation and differentiation capacity, and degree of senescence in mesenchymal stem cells is completely unknown.

The present invention is based on the result that the mesenchymal stem cells which do not express CD26 have superior proliferation and differentiation capacity compared to the mesenchymal stem cells which express CD26. That is, while the mesenchymal stem cells before size separation contain a heterogeneous group which expresses CD26, the mesenchymal stem cells of the present invention with improved proliferation and differentiation capacity have a homogeneous group which does not express CD26.

In one embodiment, the mesenchymal stem cells of the present invention can show relatively low level of CD26 expression as compared to conventional mesenchymal stem cells. The mesenchymal stem cells which do not express CD26 can be obtained by the separation process of mesenchymal stem cells not expressing CD26 from unseparated mesenchymal stem cells.

In one embodiment, the mesenchymal stem cells of the present invention with improved proliferation and differentiation capacity can express at least one selected from cluster of differentiation 49f(CD49f), cluster of differentiation 146 (CD146) and epidermal growth factor receptor(EGFR) as a cell marker.

CD49f, also known as integrin alpha-6, is a protein encoded by the ITGA6 gene in humans. Integrin is known to be related with cell adhesion and cell-surface mediated signal transduction. However, its relationship with the size, proliferation capacity and differentiation capacity of mesenchymal stem cells is completely unknown.

CD146, also known as a melanoma cell adhesion molecule (MCAM) or cell surface glycoprotein MUC18, is a cell adhesion molecule of 113kDa which is used as a marker for endothelial cells. This protein is known to function as a receptor for laminin alpha-4, a matrix molecule. However, its relationship with the size and senescence capacity of the mesenchymal stem cells is totally unknown.

EGFR is a cell-surface receptor for epidermal growth factor family of extracellular protein ligand, and the expression of EGFR or its activity variation is known to cause cancer. However, its relationship with the size, senescence capacity, proliferation capacity and differentiation capacity is absolutely unknown.

The present invention is based on the discovery that the mesenchymal stem cells which express at least one selected from CD49f, CD146 and EGFR have superior proliferation and differentiation capacity as compared to the mesenchymal stem cells which do not express any one of them.

In one embodiment, the mesenchymal stem cells of the present invention show relatively higher expression level of at least one selected from the group consisting of CD49f, CD146 and EGFR.

In another embodiment, the mesenchymal stem cells of the present invention express CD49f, CD146, and EGFR to the levels which are higher by more than 50%, more than 90% and more than 50%, respectively, as compared to the mesenchymal stem cells expressing CD26.

The mesenchymal stem cells which express at least one selected from the group consisting of CD49f, CD146 and EGFR can be obtained by a separation process of the is mesenchymal stem cells not expressing CD26 from the unseparated mesenchymal stem cells or a separation process of the mesenchymal stem cells expressing at least one selected from the group consisting of CD49f, CD146 and EGFR from the separated mesenchymal stem cells (not expressing CD26). These two processes may be conducted concurrently.

In another embodiment, the mesenchymal stem cells of the present invention with improved proliferation and differentiation capacity do not express CD26, but may express CD49f, CD146, and EGFR, as cell markers.

In one embodiment, such mesenchymal stem cells show relatively low expression level of CD26 and relatively high expression level of CD49f, CD146 and EGFR as compared to conventional mesenchymal stem cells.

In another embodiment, such mesenchymal stem cells do not express CD26, but express CD49f, CD146, and EGFR to the levels which are higher by more than 50%, more than 90% and more than 50%, respectively, as compared to the mesenchymal stem cells expressing CD26.

The mesenchymal stem cells described above may be obtained by a separation process of the mesenchymal stem cells which do not express CD26 but express CD49f, CD146 and EGFR from the unseparated mesenchymal stem cells.

The mesenchymal stem cells of the present invention may have various origins. Examples of such mesenchymal stem cells include those derived from umbilical cord blood, bone marrow, lipid, muscle, skin, amniotic fluid, umbilical cord, or teeth, but are not limited thereto. In one preferred embodiment of the present invention, the mesenchymal stem cells of the present invention can be umbilical cord blood-derived mesenchymal stem cells. In addition, the mesenchymal stem cells of the present invention may be those derived from various subjects. For example, the mesenchymal stem cells may be obtained from mammals including humans, but are not limited thereto. In one preferred embodiment of the present invention, mesenchymal stem cells of human origin may be cultured and used.

The mesenchymal stem cells of the present invention are characterized by the size is of 8 μm or less. Conventional mesenchymal stem cells are heterogeneous as they have a wide size range of 3.5 to 24 μm, which are herein referred to as mesenchymal stem cells "before size separation", "large" mesenchymal stem cells or "heterogeneous" mesenchymal stem cells. Meanwhile, the mesenchymal stem cells of the present invention are homogeneous as they have a size of 8 μm or less, which are herein referred to as mesenchymal stem cells "after size separation", "small" mesenchymal stem cells or "homogeneous" mesenchymal stem cells. The mesenchymal stem cells of the present invention show superior proliferation and differentiation capacity as compared to the mesenchymal stem cells having a size exceeding 8 μm (large).

It is preferable to separate the mesenchymal stem cells having a size of 8 μm or less by using a filter. Such filter may be selected considering the risk of damaging mesenchymal stem cells and safety in usage such as, for example, Xiaogan yaguang's filtration membrane tube. When using such filter, the filteration process may be conducted under optimum conditions for obtaining small cells. For example, mesenchymal stem cells at the population of $2\times10^5$ cells may be loaded on a filtration membrane tube having a pore size of 8 μm, and centrifuged once at 1,200 rpm for 5 minutes, to obtain homogeneous mesenchymal stem cells having a size of 8 μm or less.

The present invention also provides a method for obtaining mesenchymal stem cells having improved proliferation and differentiation capacity, comprising separating mesenchymal stem cells which do not express CD26 as a cell marker from unseparated mesenchymal stem cells.

The separation of mesenchymal stem cells can be conducted based on whether or not CD26 is expressed using a flow cytometer (fluorescence-activated cell sorting (FACS)), for example, BD FACSAria™ III sorter device.

The separation process depending on the expression of CD26 may be conducted as follows. Mesenchymal stem cells are treated with trypsin and washed with PBS solution once. The washed cells are reacted with antigen CD26-PE. The signals of secondary antibodies are detected by BD FACSAria™ III sorter device, to assess the is number of cells expressing a particular marker among the total cells. The regions where positive or negative cells are expressed at the level of 95% or higher are selected, and such positive and negative groups are separately obtained using the device.

In one embodiment, the method of the present invention can further comprise a step of separating mesenchymal stem cells which express at least one selected from the group consisting of CD49f, CD146 and EGFR as a cell marker.

Also, the present invention provides a method for obtaining mesenchymal stem cells having improved proliferation and differentiation capacity, comprising separating mesenchymal stem cells which do not express CD26 but express CD49f, CD146 and EGFR as cell markers.

The separation of mesenchymal stem cells can be conducted based on whether or not CD26, CD49f, CD146 or EGFR is expressed, using a flow cytometer (fluorescence-activated cell sorting (FACS)), for example, BD FACSAria™ III sorter device.

The separation process depending on the expression of a particular marker may be conducted as follows. Mesenchymal stem cells are treated with trypsin and washed with PBS solution once. The washed cells are reacted with each antigen of CD26-PE, CD49f-Alexa® 647, CD146-FITC and EGFR-PE. The signals of secondary antibodies are detected by BD FACSAria™ III sorter device, to assess the number of cells expressing a particular marker among the total cells. The regions where positive or negative cells are expressed at the level of 95% or higher are selected, and such positive and negative groups are separately obtained using the device.

The mesenchymal stem cells obtained according to the present invention can be utilized for the regeneration of pulmonary cells, and are useful for the prevention or treatment of a pulmonary disorder including pulmonary emphysema.

Hereinafter, the present invention is explained in detail by Examples. The is following Examples are intended to further illustrate the present invention without limiting its scope.

EXAMPLE 1

Analysis of Cell Size of Mesenchymal Stem Cells Derived From Various Tissues

For the analysis of cell size of mesenchymal stem cells derived from various tissues, each of the cryopreserved collections of mesenchymal stem cells, such as bone marrow-derived mesenchymal stem cells (referred to as 'BM'; Cambrex, Walkerville, Md., USA), adipose tissue-derived mesenchymal stem cells (referred to as 'AT'; ATCC, Rockville, Md., USA), and umbilical cord blood-derived mesenchymal stem cells (referred to as 'UCB'; Medipost, Korea) was thawed, and cultured in an incubator having α-MEM medium supplemented with 10% FBS (Invitrogen, Calsbad, Calif., USA), under the condition of 37° C. and 5% $CO_2$ for 5 days.

The morphology of the cells was observed with a microscope, and single cells were obtained by treatment with trypsin. The single cells were treated with trypan blue to examine survival rate. The cells were observed with ECLIPSE TE2000-U inverse microscope (Nikon) at 100× magnification, and multiple regions of the cell population were photographed. At the photographed regions, the size of live cells was analyzed using Cellometer vision 5× (nexcelom biosceince).

Figure 1C:
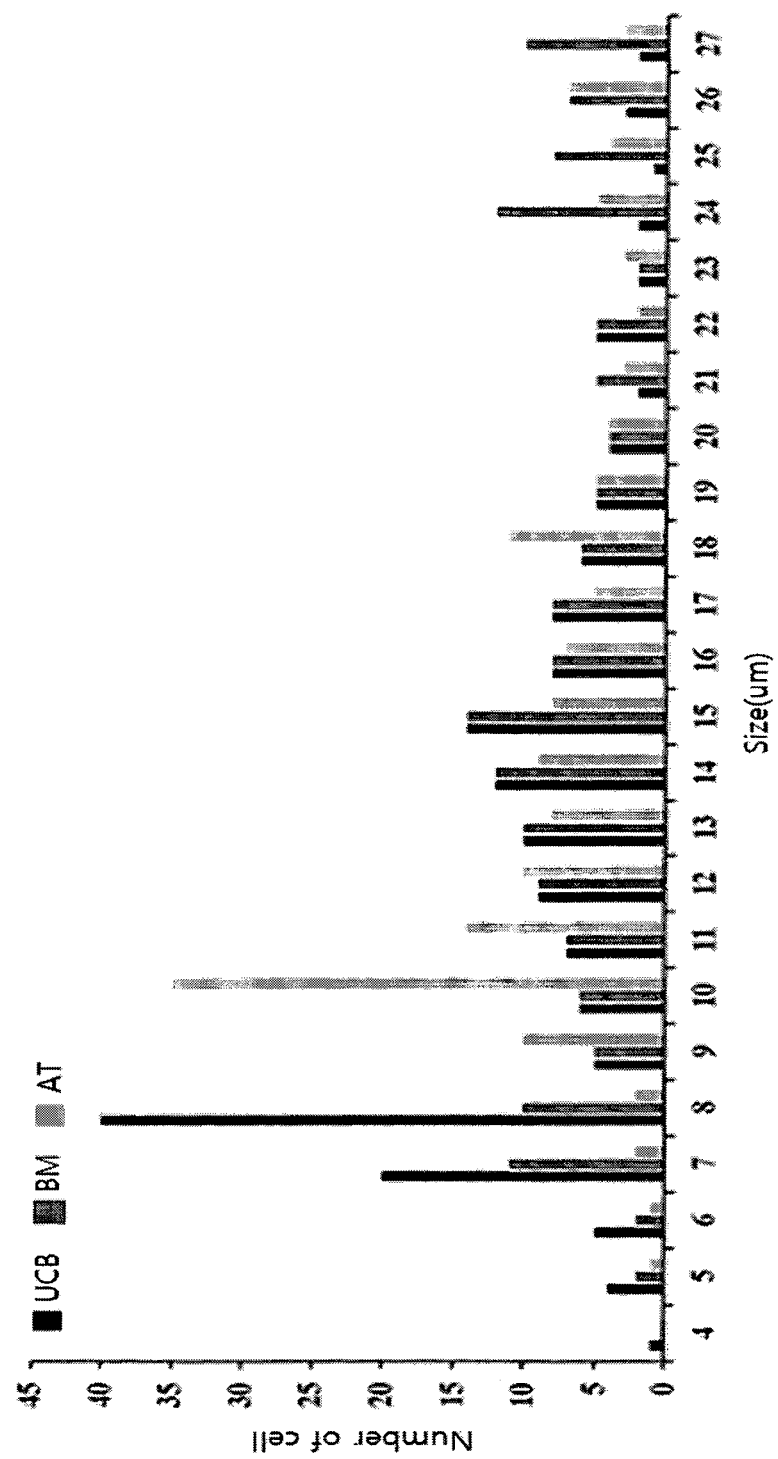

FIGS. 1A and 1B are microscopic photographs showing cultured mesenchymal stem cells, and mesenchymal stem cells in the form of single cells after trypsinization, respectively. FIG. 1C is a graph showing the results of measurement of the cell size.

As can be seen in FIGS. 1A to 1C, no information on cell size could be obtained when the cells were adherent to each other (FIG. 1A), but cell size could be examined when the cells were in the form of single cells (FIG. 1B). Upon analysis with Cellometer, it was found that each population of the mesenchymal stem cells derived from bone marrow, fat, and umbilical cord constitute a heterogeneous population of cells with various sizes (FIG. 1C). And the size of umbilical cord blood-derived mesenchymal stem cells was found to be smaller than mesenchymal stem cell derived from bone marrow or fat.

EXAMPLE 2

Analysis of Proliferative Capacity of Umbilical Cord Blood-Derived Mesenchymal Stem Cells According to Their Size To analyze the correlation between the cell size and the proliferative capacity, the umbilical cord blood-derived mesenchymal stem cells were divided into 5 groups based on the ratio of the cells having a size of 8 μm or less to the total cells as in Table 1.

TABLE 1

| Group | Ratio of cells having a size of 8 μm or less |
|---|---|
| Group 1 (G1) | 1-10% |
| Group 2 (G2) | 11-20% |
| Group 3 (G3) | 21-30% |
| Group 4 (G4) | 31-40% |
| Group 5 (G5) | 41-50% |

The cells of G1 to G5 were cultured with passages, and cumulative growth curves were prepared. The cumulative growth curve was expressed as cumulative population doubling (CPD) which is a cumulative value of population doubling (PD).

The PD was calculated based on a total number of cells of each passage, which was log (proliferation rate of a specific passage)/log 2. When cells of a specific passage reached 50 to 60% of confluence, they were trypsinized and separated, to harvest single cells. The proliferation rate of a specific passage was calculated by dividing the number of the harvested single cells by the number of cells which had been initially provided to the culture vessel. These procedures were repeated until a passage at which proliferation of cells stopped. Cells were allowed to proliferate starting from the first and second passages until the last passage at which proliferation of cells stopped. The period of culture per passage was 7 days. P1 to P10 in the graph refers to the number of passages. The experimental results are shown in FIG. 2.

Figure 2:
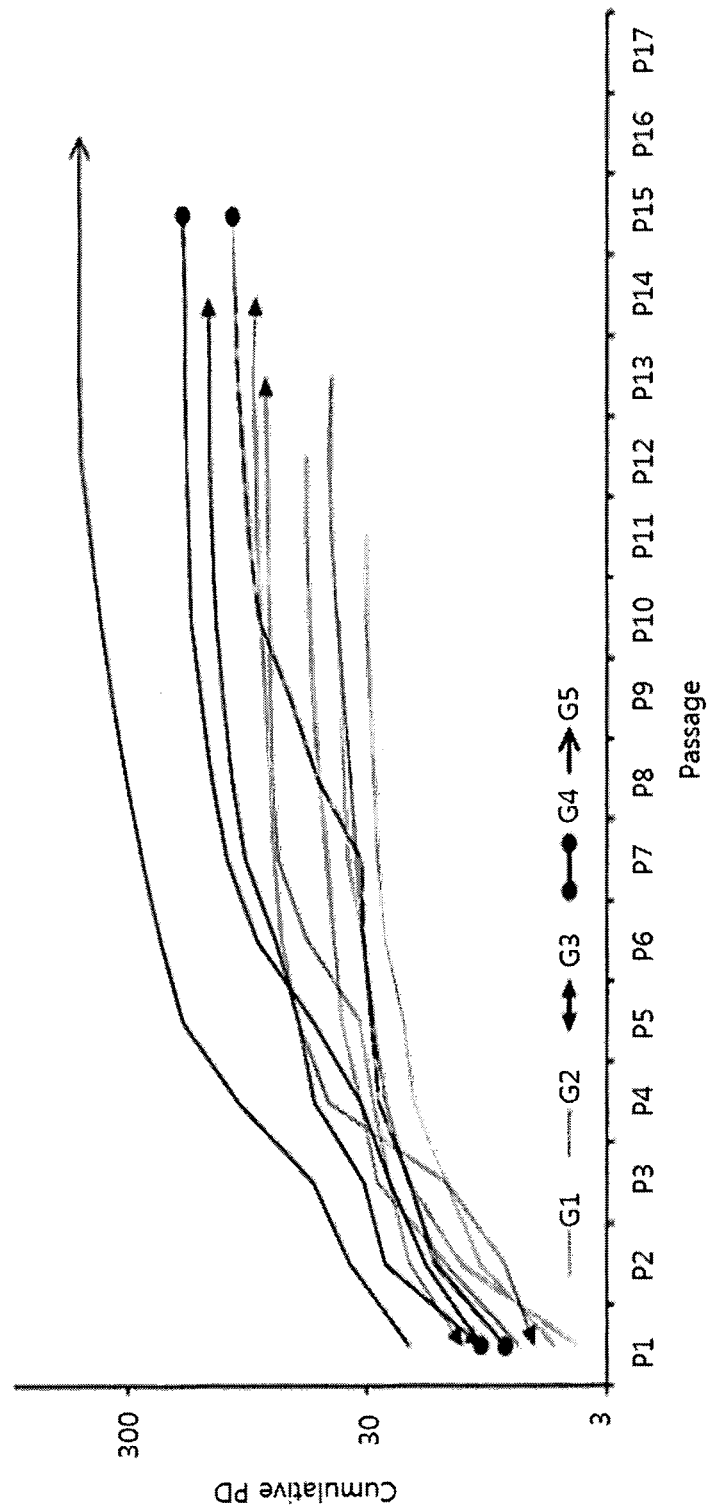
FIG. 2 shows cumulative population doubling (CPD) of the umbilical cord blood-derived mesenchymal stem cells of the groups with different cell sizes (G1 to G5) after culturing each group with passages.

As can be seen from FIG. 2, the proliferation capacity was higher in the group in which the ratio of cells having a size of 8μm or less was higher.

EXAMPLE 3

Determination of Cell Size and Separation of Small Cells

<3-1> Determination of cell size suitable for separation

As a filter for analyzing cells according to their size, Xiaogan yaguang's filtration membrane tube was selected.

The filter can be protected from contamination from outside during centrifugation, owing to its installation inside a 50 ml tube. Meanwhile, equipments for separating cells are known, such as sorting equipment, Beckman's high speed centrifuge, BD's Transwell® and the like. But, the sorting equipment is not suitable for a procedure of manufacturing therapeutic agents due to possibility of damaging cells during a separation process of cells. Beckman's high-speed centrifuge equipment is not suitable for use in a GMP manufacturing process because it does not utilize disposable products for consumable parts. As for Transwell®, not being a sealed system, it does not guarantee aseptic condition of cells during centrifugation. Considering that the mesenchymal stem cells of the present invention should be used as a therapeutic agent, Xiaogan yaguang's filtration membrane tube suitable for the actual GMP manufacturing facility was determined to be best suited.

Using the filtration membrane tube, umbilical cord blood-derived mesenchymal stem cells having a size of 3 μm or less (≤3 μm), 5 μm or less (≤5 μm), and 8 μm or less (≤8 μm) were separated. The amount of each of the separated cell group was measured. As a result, the amount of the cells having a size of ≤3 μm or ≤5 μm separated by the filter, as well as the percentage of said cells among mesenchymal stem cell population, was too low. In contrast, the mesenchymal stem cells having a size of ≤8 μm were obtained in a sufficient amount. As such, a suitable cell size was determined to be 8 μm or less, and the cells of this size range were referred to as "small cells" or "small mesenchymal stem cells."

<3-2> Separation of Small Cells

Figure 3:
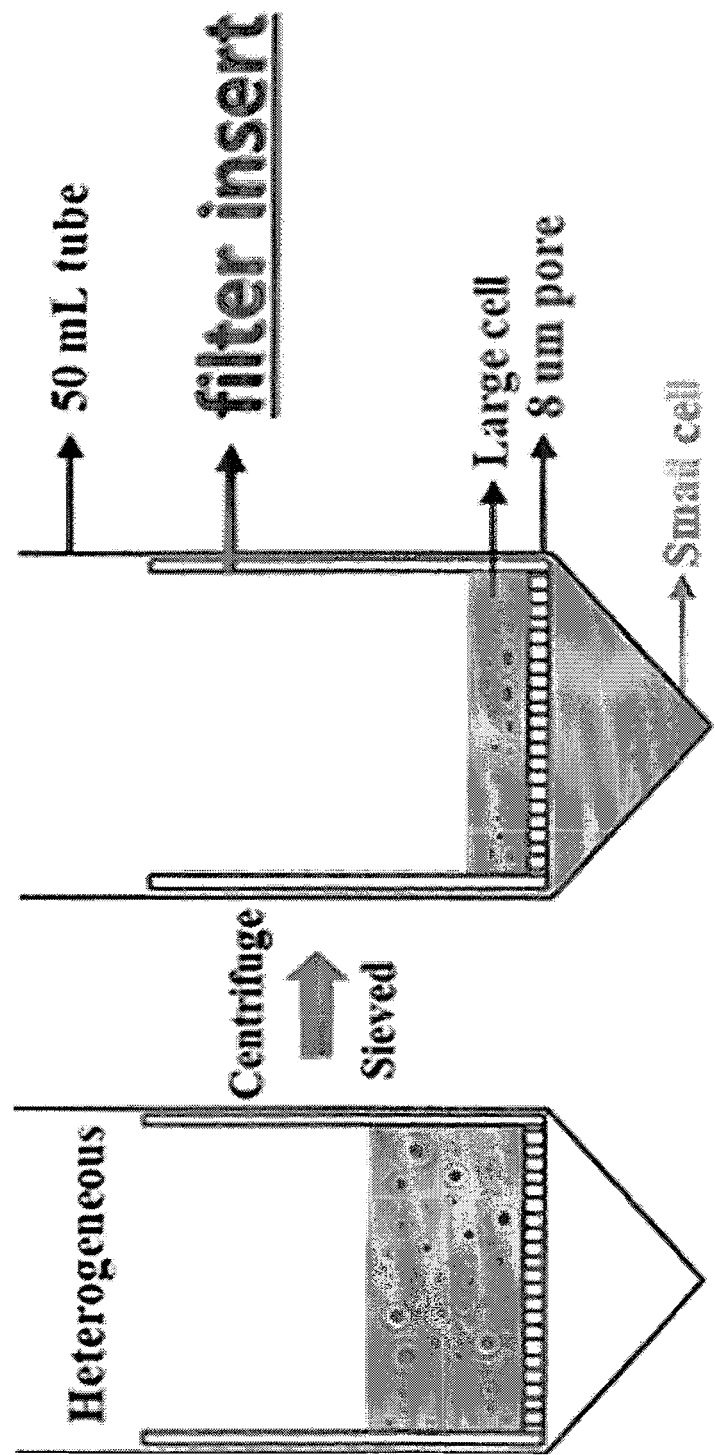
FIG. 3 is a schematic diagram showing the separation process of mesenchymal stem cells having a size of 8 μm or less.

After thawing the umbilical cord blood-derived mesenchymal stem cells cryopreserved in liquid nitrogen, the cells were cultured in an incubator containing α-MEM medium supplemented with 10% FBS under the condition of 37° C. and 5% $CO_2$ until reaching 50-60% confluency. After detaching the cultured mesenchymal stem cells with trypsin, $2 \times 10^5$ of the mesenchymal stem cells were suspended in 2 ml of α-MEM medium supplemented with 10% FBS, which were then loaded on a filter membrane tube having a pore size of 8 μm (Universal Filtration membrane cartridge tube). Then, the filter membrane tube was centrifuged at 1,200 rpm for 5 minutes to obtain a homogeneous group of cells having a size of 8 μm or less (see FIG. 3).

EXAMPLE 4

Comparison of Features According to Size Separation

To examine the features of mesenchymal stem cells obtained by the aforementioned size separation, comparative analysis of the features were carried out with regard to mesenchymal stem cells before and after size separation as below.

<4-1> Morphological Feature

The mesenchymal stem cells before and after size separation were observed under a microscope. The results are shown in FIG. 4.

Figure 4:
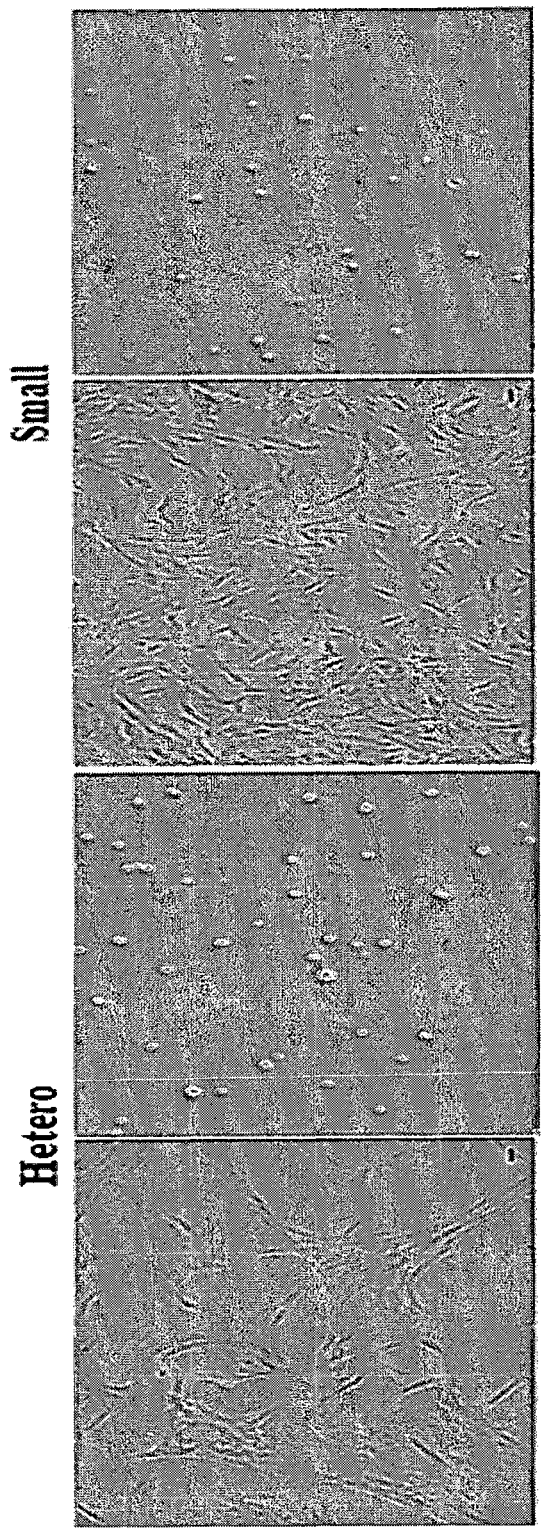
FIG. 4 provides microscopic photographs of mesenchymal stem cells before (Hetero) and after (Small) size separation.

As can be seen in FIG. 4, there was no change in morphological features between the mesenchymal stem cells before and after size separation. It was confirmed that a uniform cell population having a size of 8 μm or less was obtained by the size separation according to the present invention.

<4-2> Analysis of Markers

To analyze the immunophenotypes of cell surface antigens in mesenchymal stem cells before and after size separation, the expressions of marker proteins (CD14, CD34, CD45, HLA-DR, CD29, CD44, CD90, CD105, HLA-ABC) were examined by FACS analysis as following.

Mesenchymal stem cells before and after size separation were cultured separately. Then, the cells were treated with trypsin and washed once with PBS solution. The washed cells were reacted with CD14-FITC (fluorescein isothiocyanate), CD34-FITC, CD45-FITC and HLA-DR-FITC, known negative antigens in mesenchymal stem cells, and with CD29-PE (phycoerythrin), CD44-PE, CD9O-PE, CD105-PE and HLA-ABC-PE, known positive antigens strongly expressed in mesenchymal stem cells. The ratio of cells expressing the markers to the total cells was obtained by detecting signals of secondary antibodies by FACS machine. Analysis after the reaction was conducted using FACSCalibur flow cytometer (Becton Dickinson, San Jose, Calif., USA) and CELLQUEST software.

The experimental results are shown in Table 2.

TABLE 2

| Markers | CD14 | CD34 | CD45 | HLA-DR | CD29 | CD44 | CD90 | CD105 | HLA-ABC |
|---|---|---|---|---|---|---|---|---|---|
| Cells before size separation | − | − | − | − | + | + | + | + | + |
| Cells after size separation | − | − | − | − | + | + | + | + | + |

As can be seen in Table 2, there is no difference the expression of marker in mesenchymal stem cells before and after size separation.

<4-3> Osteogenic Induction and Bone Staining

To compare the osteogenic differentiation capacity, which is known as a characteristic feature of mesenchymal stem cells, the mesenchymal stem cells before and after size separation were each placed in 6-well plates at 500-1000 cells/well, and an osteogenic induction medium (10 mM glycerol phosphate, 50 mM L-ascorbic acid-2-phosphate, 1 μM dexamethasone/UVAB, α-MEM medium supplemented with gentamycin and 10% FBS) was provided after 2-4 days. The medium was replaced with new differentiation medium every 3 days to induce differentiation of the cells for 2-3 weeks. The differentiated cells were washed twice with PBS and then incubated in a fixation solution (40% acetone) for 30 to 45 seconds. After washing the cells 2-3 times with distilled water, an alkaline dyeing solution (Fast violet B salt) was added thereto, and the cells were cultured in a dark place at room temperature for 30 minutes. Then the cells were washed twice with distilled water, and treated with Mayer's Hematoxylin solution for 10 to 20 seconds. After removing the solution, the cells were washed with tap water and dried. The stained tissues were covered with a cover slide using an aqueous mounting solution for observation.

Because cells which have differentiated into osteoblasts are stained dark brown due to activation of intra-cellular alkaline phosphatase, the degree of osteogenic induction of the cells was evaluated based on the degree of staining The results are shown in the left part of FIG. 5. As can be seen in FIG. 5, the small mesenchymal stem cells obtained after size separation according to the present invention showed superior osteogenic differentiation capacity compared to the mesenchymal stem cells before size separation.

<4-4> Chondrogenic Differentiation Induction and Cartilage Staining

To compare the chondrogenic differentiation capacity, which is known as a characteristic feature of mesenchymal stem cells, the cells of each group were place in 15 ml conical tubes at $2-2.5\times10^5$ cells per tube. Then, cells were obtained by centrifugation, washed once with PBS, suspended in 200-250 μl of chondrogenic differentiation medium (DMEM medium supplemented with 10 ng/ml TGF-β3, 500 ng/ml BMP-6, 50 μg/ml ascorbic acid, 50 mg/ml (1:100) ITS-premix, 40 μg/ml L-proline, 100 μg/ml sodium pyruvate, 100 nM dexamethasone/UVAB, and gentamicin), and then placed in tubes. The tubes were centrifuged at 1500 rpm for 5 minutes, and differentiation was induced in $CO_2$ incubator with the lid slightly open at 37° C. for 4 weeks. Half of the differentiation medium was replaced twice a week. The differentiated cells were centrifuged, washed with PBS, and fixed with para-formaldehyde at room temperature for 30 minutes to 1 hour. After washing the cells 2-3 times with distilled water, sections (thickness: 4-5 μm) were prepared by a frozen section method. The sections were put into 95% ethanol for 3-5 minutes, washed twice with water, and stained by dipping them in 0.1% safranin-O solution for 7 minutes. After staining, the sections were washed twice with 70% ethanol, once with 70% ethanol, twice with 95% ethanol, once with 95% ethanol and twice with 100% is ethanol; dipped in a xylene substrate solution for 3 minutes; and dried. After drying, the stained tissues were covered with a fat-soluble mounting solution and observed. The degree of chondrogenic differentiation was evaluated by comparing the intensity of a stained color (orange), the size of the finally differentiated pellet and the degree of lacuna structure formation.

The results are shown in the middle part of FIG. 5. As can be seen in FIG. 5, the chondrogenic differentiation capacity of the small mesenchymal stem cells after size separation of the present invention was similar to the mesenchymal stem cells before size separation.

<4-5> Adipogenic Induction and Fat Staining

To compare the adipogenic differentiation capacity, which is known as a characteristic feature of mesenchymal stem cells, the mesenchymal stem cells before and after size separation were each placed in 6-well plates at 500-1000 cells/well, and an adipogenic induction medium (0.5 mM 3-isobutyl-1-methyl xanthine, 0.2 mM indomethacin, 10 μM insulin, 1 μM dexamethasone/UVAB, and DMEM medium supplemented with 10% FBS and gentamicin) was provided after 2-4 days. The medium was replaced with new differentiation medium every 3 days to induce differentiation for 3-4 weeks. The differentiated cells were washed twice with PBS and then incubated in a fixation solution (10% formalin) for 10 minutes. After washing the cells 2-3 times with distilled water, a staining solution (oil red O) was added thereto, and the cells were placed at room temperature for 30 minutes. Then, the cells were washed with distilled water and treated with Mayer's Hematoxylin solution for 10 to 20 seconds. After removing the solution, the cells were washed with tap water and dried. The stained tissues were observed, covered with a cover slide while using an aqueous mounting solution. The degree of adipogenic differentiation was evaluated based on the degree of staining (red), and the degree of formation of the finally differentiated lipid vacuoles.

The experimental results are shown in the right part of FIG. 5. As can be seen in FIG. 5, the adipogenic differentiation capacity in small mesenchymal stem cells is obtained after size separation according to the present invention was similar to the mesenchymal stem cells before size separation.

<4-6> Comparison of Proliferation Capacity

To compare the proliferation capacity between the mesenchymal stem cells before and after size separation, mesenchymal stem cells (MSCs1 & MSCs2) obtained from two donors were subjected to size separation according to the method of the present invention, and then cultured with passages for comparison of the proliferation capacity. The two groups of cells were cultured in α-MEM medium supplemented with 10% FBS, for 5 days per passage, to measure their cumulative growth.

The measurement results are shown in FIG. 6. As can be seen in FIG. 6, the proliferation capacity of mesenchymal stem cells after size separation was far superior to mesenchymal stem cells before size separation.

<4-7> Comparison of Senescence Capacity

To compare the senescence capacity between the mesenchymal stem cells before and after size separation, the mesenchymal stem cells before and after size separation were cultured up to passage 9. Then culture solution was removed from each culture vessel and cells were washed once with PBS. Then, after adding 1 ml of 1× fixation solution (Cell Signaling Technology) thereto, the cells were cultured for 10 minutes at room temperature. After removing the fixation solution, the cells were washed twice with 2 ml of PBS. Next, after adding 1 ml of a β-galactosidase staining solution (SA β gal, Cell Signaling Technology) thereto, the cells were cultured in the incubator for 24 to 48 hours. And then, after removing the staining solution, the cells were washed with 1 ml of PBS. Then, the stained cells were photographed using ECLIPSE TE2000-U inverse microscope (Nikon) at 100× magnification.

Figure 7A:
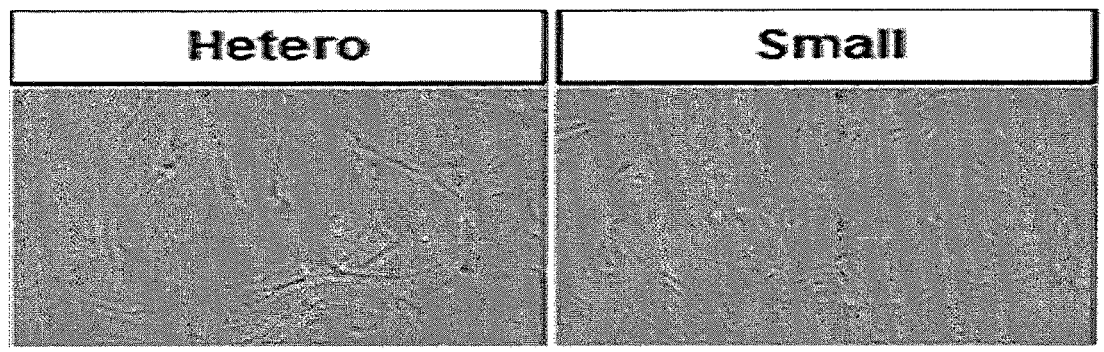
FIGS. 7A and 7B are photographs showing the senescence-related staining (FIG. 7A) and the activity of senescence-related proteins examined by Western blot (FIG. 7B) of the mesenchymal stem cells before and after size separation which were each cultured with several passages to induce senescence.

The results are shown in FIG. 7A. As can be seen in FIG. 7A, the blue stained area in mesenchymal stem cells after size separation was relatively smaller than mesenchymal stem cells before size separation, indicating inhibition of senescence.

Meanwhile, the cells at passage 9 were detached by treatment with trypsin. Subsequently, cell culture solution was centrifuged to remove the medium, and then was washed with PBS to obtain cells. Next, protein was isolated from the cells using a lysis buffer (RIPA; Thermo Scientific, Rockford, Ill., USA) according to the manufacturer's protocol. The protein was quantified using bovine serum albumin (BSA) as a standard, and 15 μg of the protein was prepared to perform Western blot. The protein was loaded onto 12% polyacrylamide gel, and then was electrophoresed at 130 V for 2 hours. After the electrophoresis, the protein was transferred from the gel to a nitrocellulose membrane (Amersham Pharmacia, USA) with a current of 300 mA for 3 hours using Western Blotter, and the membrane was blocked for 1 hour using 1× TBST (100 mM Tris (pH 7.5), 1.5 M NaCl, 0.5% Tween-20) solution containing 5% fat-free milk. Then, primary antibodies (P-p53, p21, P16, p-Rb (Cell Signaling, Danvers, Mass., USA) and β-actin (Sigma-Aldrich, St. Louis, Mo., USA)) were attached to the blocked nitrocellulose membrane, at a refrigeration temperature overnight. Thereafter, the resultant nitrocellulose membrane was washed with 1× TBST, and secondary antibodies (anti-rabbit IgG HRP secondary antibody; AbClon, Guro-dong, Seoul, Korea) were added and allowed to attach thereto for 1 hour at room temperature. Next, ECL prime solution was poured on the membrane by using ECL Western blotting detection kit (Amersham Pharmacia) according to the manufacturer's protocol and bands were examined by Chemidoc equipment (Biorad, USA).

Figure 7B:
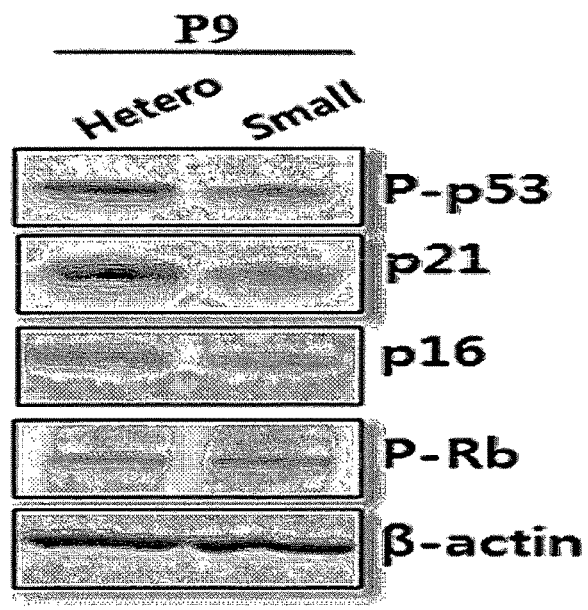

The Western blot results are shown in FIG. 7B. As can be seen in FIG. 7B, the activities of the senescence-related proteins (P-p53, p21, p16, P-Rb (Abcam, USA)) in mesenchymal stem cells after size separation were relatively lower than mesenchymal stem cells before size separation. These results indicate that small cells of the present invention have excellent senescence inhibition capacity.

<4-8> Comparison of Stem Cell Capacity

To compare the stem cell capacity between the mesenchymal stem cells before and after size separation, the expression levels of Nanog and Oct4, known representative stem cell capacity genes, were measured.

Specifically, the mesenchymal stem cells of each group were centrifuged to remove medium, washed with PBS, and then centrifuged again to obtain cells. The process was repeated twice to remove all the PBS remaining in the cells. Then, using a RNA isolation kit (Invitrogen), RNA was isolated according to the manufacturer's protocol. After synthesizing a template cDNA from the RNA using SuperScript™ III (Invitrogen) reverse transcriptase, a real-time PCR was carried out using specific primers for the stem cell markers GAPDH, Oct4 and Nanog (CosmogeneTech, see Table 3).

A PCR reaction (10 minutes at 95° C., 10 seconds at 95° C., 30 seconds at 62° C., and 10 seconds at 72° C.) was repeatedly performed for 40 cycles using LightCycler 480 Real-Time PCR System instrument (Roche).

TABLE 3

| Markers | Sequences (F: forward, R: reverse) |
|---|---|
| Oct4 | F: CAATTTGCCAAGCTCCTGA (Sequence ID number: 1) R: CGTTTGGCTGAATACCTTCC (Sequence ID number: 2) |
| Nanog | F: AGATGCCTCACACGGAGACT (Sequence ID number: 3) R: TTTGCGACACTCTTCTCTGC (Sequence ID number : 4) |
| GADPH | F: AGCCACCATCGCTCAGACAC (Sequence ID number: 5) R: GCCCAATACGACCAAATCC (Sequence ID number: 6) |

Figure 8:
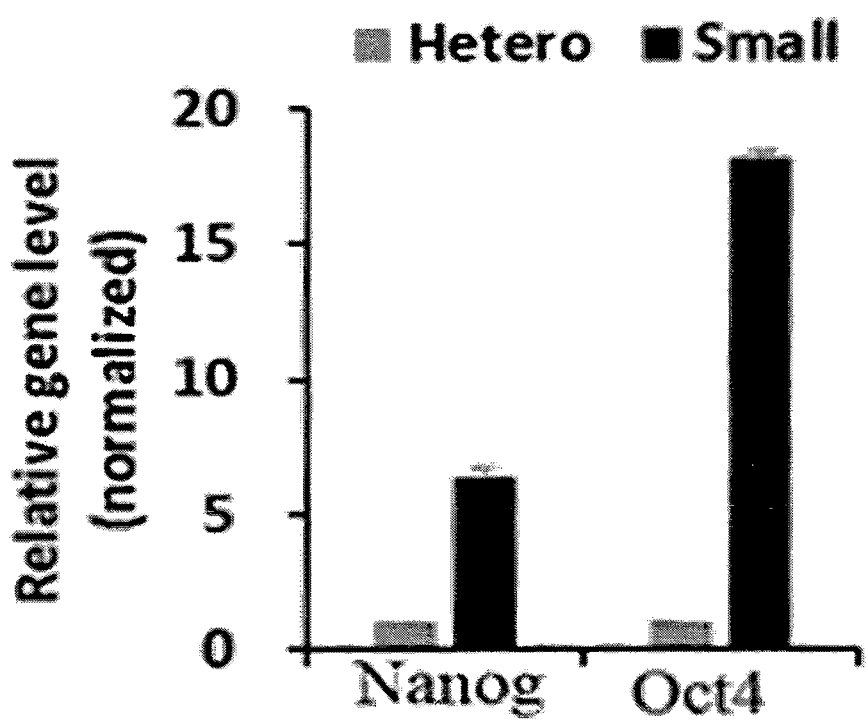
FIG. 8 is a graph showing the expression levels of stem cell capacity genes in the mesenchymal stem cells before and after size separation.

The measurement results are shown in FIG. 8. As can be seen in FIG. 8, the expression levels of Nanog and Oct4 genes in the small mesenchymal stem cells after size separation were relatively higher. The result indicates that the stem cell capacity of the mesenchymal stem cells after size separation of the present invention are far superior to the mesenchymal stem cells before size separation.

<4-9> Comparison of Cell Adhesion Capacity

To determine the flask adhesion capacity according to cell size, the cells of each group were inoculated into two flasks at 2000 cells/cm$^2$. At 6, 12, 18 and 24 hours after the inoculation, 6 or more photographs of a cellular region attached to the bottom of the flask were taken at 100× microscope magnification in each group using Incucyte Zoom (ESSEN bioscience, Ann Arbor, Mich., USA), which were then automatically is quantitated.

Figure 9:
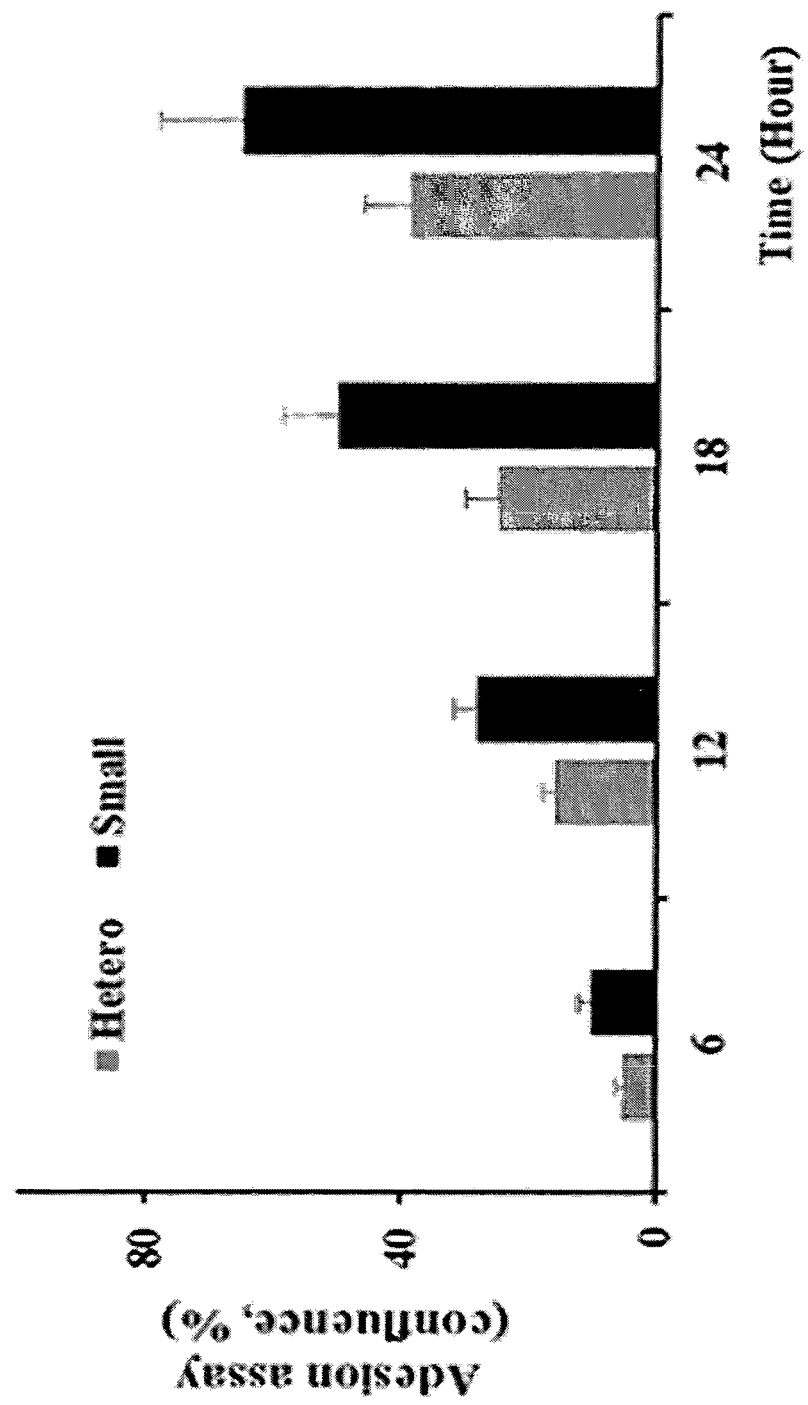
FIG. 9 is a graph showing the cell adhesion capacity of mesenchymal stem cells before and after size separation.

The results are shown in FIG. 9. As can be seen in FIG. 9, the cell adhesion capacity of mesenchymal stem cells after size separation of the present invention was superior to mesenchymal stem cells before size separation.

To summarize, these results of Example 4 indicate that the small mesenchymal stem cells obtained by a method of the present invention have excellent capacity of proliferation, stem cell, adhesion and osteogenic differentiation; and show low level of senescence.

EXAMPLE 5

Selection of Cell Markers Representing Mesenchymal Stem Cell Having a Size of 8 μm or less (small cell)

<5-1> Selection of Cell Marker Candidates

To screen for the cell markers which can represent a mesenchymal stem cell having a size of 8 μm or less, mesenchymal stem cells before and after size separation were each placed in 96-well plates at 5×10$^5$ cells/well. Then, according to the protocol of Human cell surface marker screening panel (BD Lysoplate, BD Biosciences, San Diego, Calif., USA), a total of 242 markers were put into each well and reacted for 20 minutes. Cells in each well were washed once with PBS, added with a secondary antibody Alexa Fluor® 647, and then reacted for 20 minutes. Comparative analysis of their expressions was conducted using FACS device.

Figure 10:
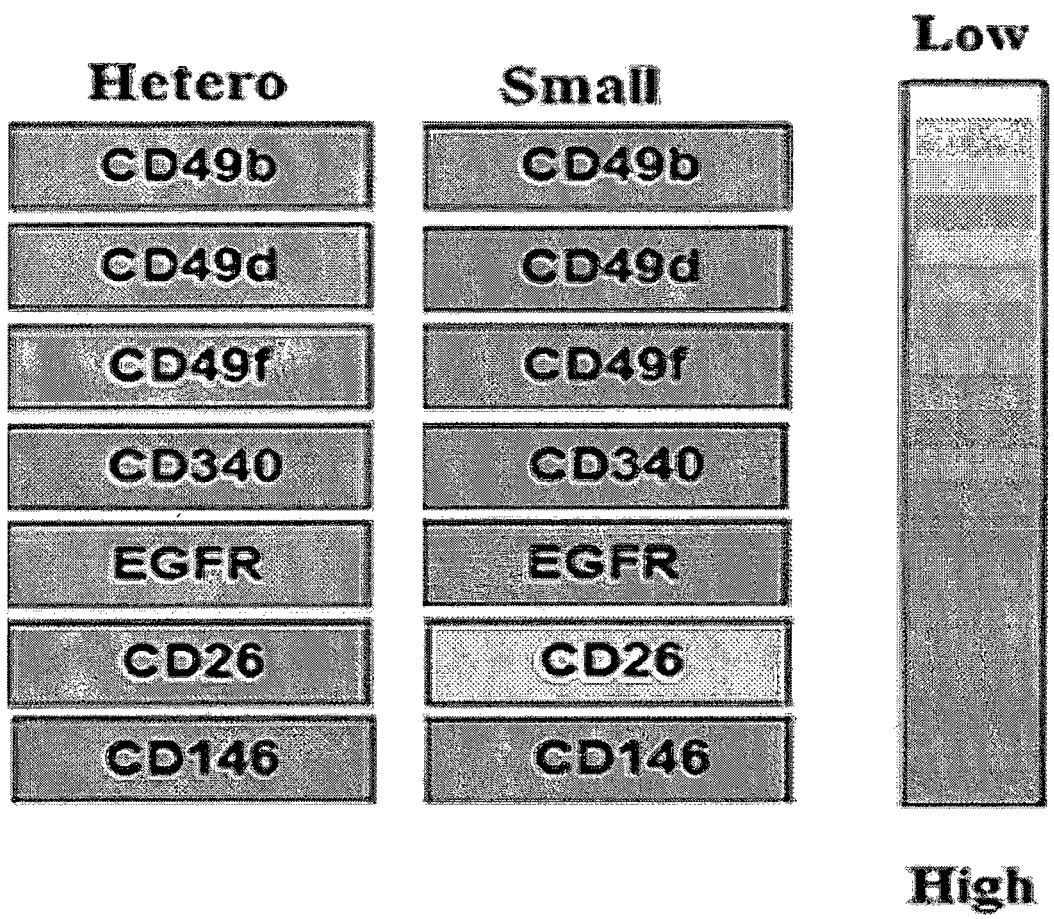
FIG. 10 is an analysis result showing the differences in the expression levels of 7 kinds of cell markers in mesenchymal stem cells before and after size separation.

As a result, 7 out of 242 markers were selected as the candidates. The expression results of the selected markers are shown in FIG. 10.

<5-2> Verification of Cell Marker Candidates

The expression levels of the 7 kinds of cell marker candidates selected in the Example <5-1>were measured with regard to the mesenchymal stem cells before and after size separation. Specifically, the cells were reacted with CD26-PE, CD49b-PE, CD49d-APC, CD49f-Alexa® 647, CD146-FITC, CD340-APC, and EGFR-FITC antibody. By detecting the signals of secondary antibodies with FACS device, the ratios of cells expressing a particular marker to the total cells were obtained. For the analysis after the reaction, FACSCalibur flow cytometer and CELLQUEST software were used.

As a result, there were differences in the expression levels of CD26, CD49f, CD146 and EFGR. These 4 kinds of cell markers were selected as the cell markers representing a mesenchymal stem cell after size separation. The comparative analysis result of expression levels of the 4 kinds of cell markers is shown in FIG. 11.

Figure 11:
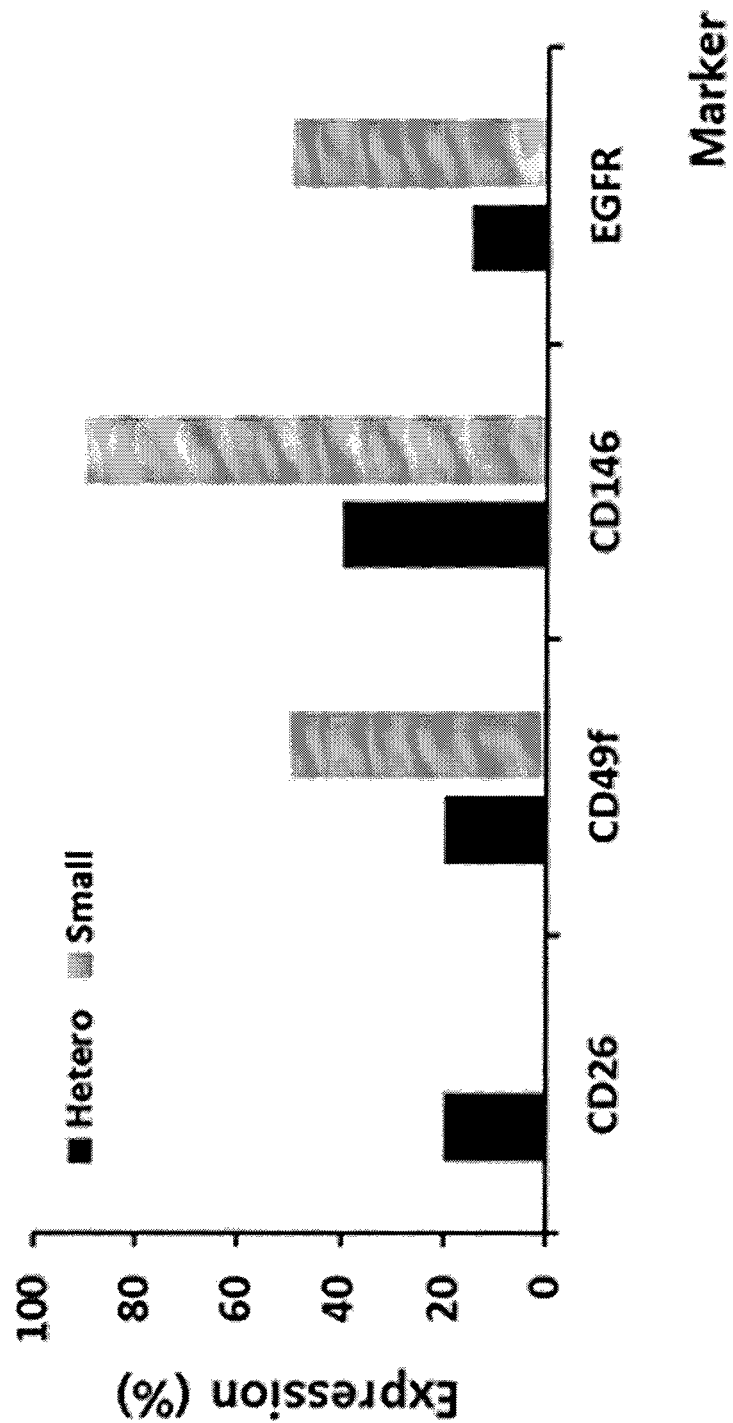
FIG. 11 is a graph showing the expression levels of CD26, CD49f, CD146 and EGFR in mesenchymal stem cells before and after size separation.

As can be seen in FIG. 11, the small mesenchymal stem cells after size separation of the present invention did not express CD26, whereas they expressed CD49f, CD146 and EGFR to the levels which were much higher than mesenchymal stem cells before size separation.

EXAMPLE 6

Cell Separation Depending on CD146 Expression and Feature Analysis

<6-1> Cell Separation Depending on CD146 Expression

Based on the results of Example 5, mesenchymal stem cells were divided into those which express CD146 and those which do not.

Specifically, the umbilical cord blood-derived mesenchymal stem cells were separated into a cell group which expresses CD146 (CD146+; positive cell group) and the other cell group which does not express CD146 (CD146−; negative cell group), using BD FACSAria™ III sorter device (BD Bioscience, Calif., USA). The mesenchymal stem cells of each group were treated with trypsin and washed once with PBS solution. The washed cells were reacted with each antigen CD146-FITC. The signals of secondary antibodies were detected by BD FACSAria™ III sorter device, to assess the number of cells expressing a particular marker among the total cells. The regions where positive or negative cells were expressed at the level of 95% or higher were selected, and positive and negative groups were separately obtained using a device. The purity of each of the separated cell groups was assessed and only the cell group with 95% or higher purity was used in further experiments.

<6-2> Feature Analysis

Comparative analysis of the cell size, shape, osteogenic differentiation capacity, proliferation capacity, and senescence capacity was conducted with regard to the above two cell groups separated in Example <6-1>(a cell group which expresses CD146 and the other cell group which does not).

(a) Comparison of morphological features

The size and shape of each cell were observed with a microscope.

Figure 12:
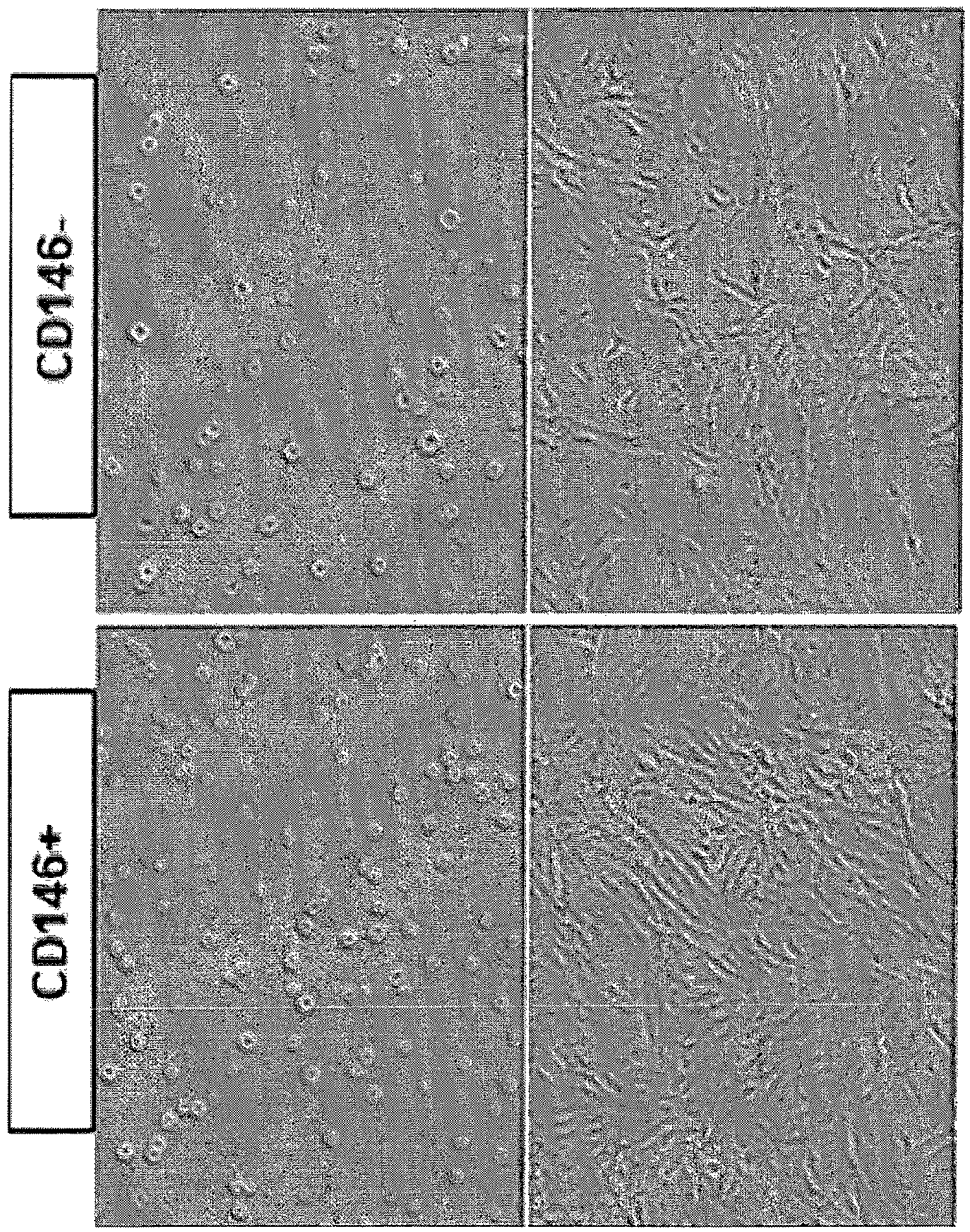
FIG. 12 provides microscopic photographs of the cells which express CD146 and those which do not, in a suspension state (upper part) and an adhesion state (lower part).

The results are shown in FIG. 12. FIG. 12 provides photographs showing the cells which express CD146 and those which do not, in a suspension state (upper part) and an adhesion state (lower part). As can be seen in FIG. 12, there could be found no remarkable differences in shape between the two groups, but the size of the cells expressing CD146 was found to be smaller.

(b) Comparison of osteogenic differentiation capacity

The osteogenic differentiation capacity of each cell group was analyzed by the same method as Example <4-3>.

Figure 13:
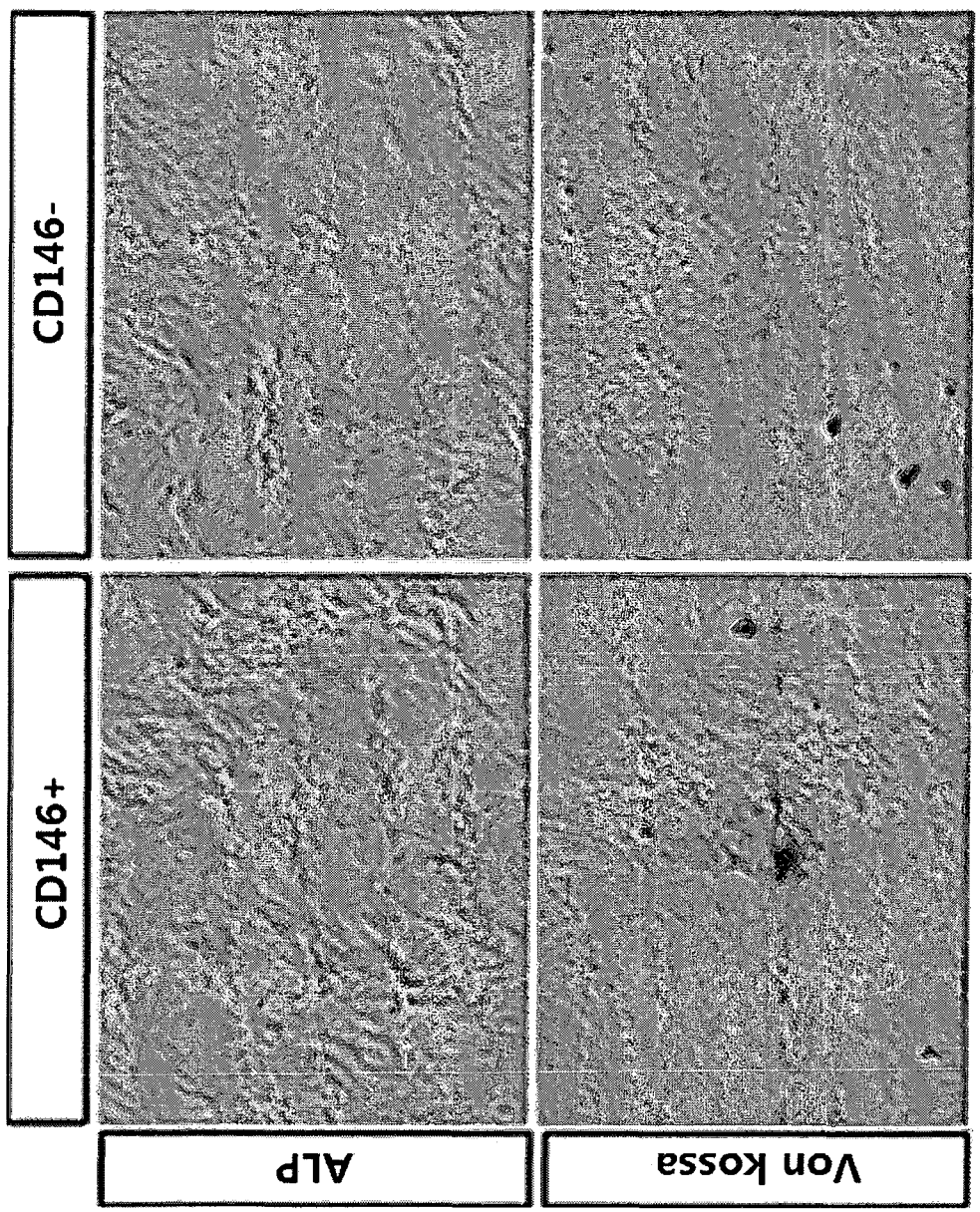
FIG. 13 provides photographs showing the osteogenic differentiation capacity of the cells which express CD146 and those which do not.

The results are shown in FIG. 13. As can be seen in FIG. 13, the osteogenic differentiation capacity of the cells expressing CD146 was superior.

(c) Comparison of proliferation capacity

The mesenchymal stem cells at passage 5 were separated based on whether CD146 was expressed or not. And the proliferation capacity of each cell group was analyzed by the same method as Example <4-6>.

Figure 14:
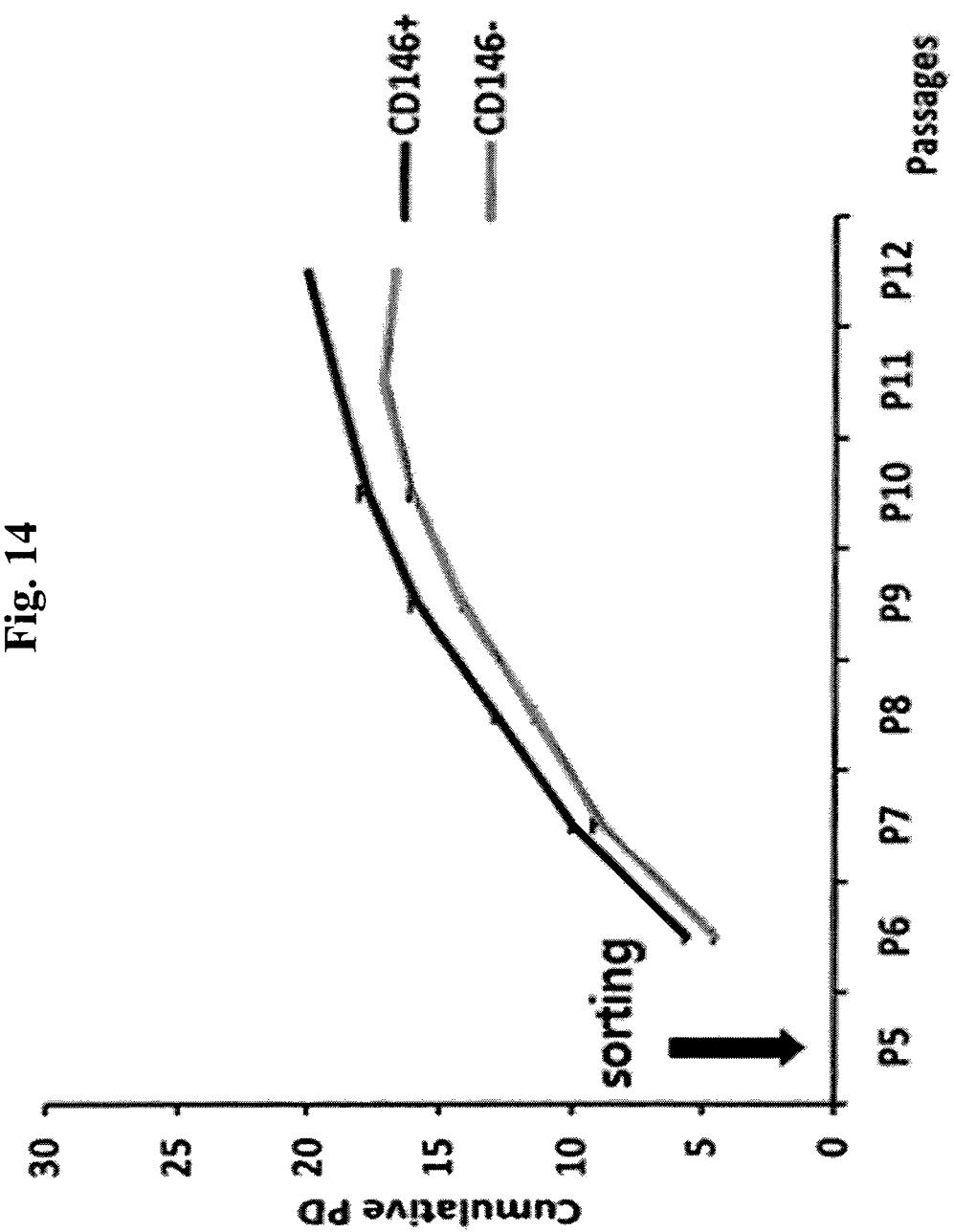
FIG. 14 is a graph showing CPD of the cells which express CD146 and those which do not.

The results are shown in FIG. 14. As can be seen in FIG. 14, the proliferation capacity of the cells expressing CD146 was superior.

(d) Comparison of senescence

The senescence capacity of each cell group was analyzed by the same method as Example <4-7>.

Figure 15A:
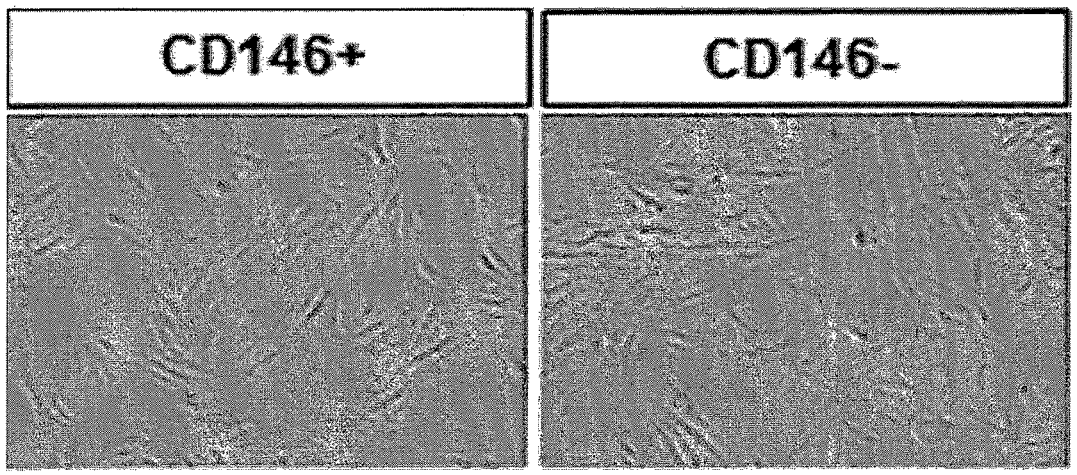
FIGS. 15A and 15B are photographs of the cells which express CD146 and those which do not, showing senescence-related staining (FIG. 15A), and the activity of senescence-related proteins examined by Western blot (FIG. 15B).
Figure 15B:
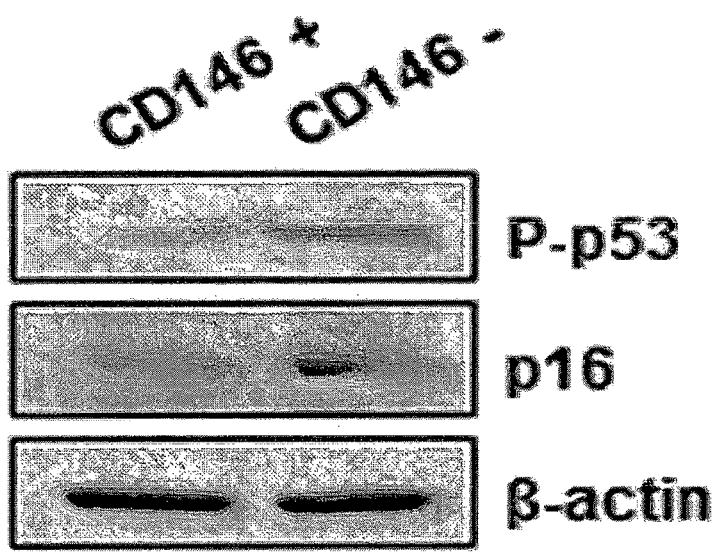

The results are shown in FIGS. 15A and 15B. As can be seen in FIGS. 15A and 15B, the expression levels of senescence-related proteins were lower in the cells expressing CD146, indicating an excellent senescence inhibition capacity.

EXAMPLE 7

Cell Separation Depending on CD26 Expression and Feature Analysis

<7-1> Cell Separation Depending on CD26 Expression

Based on the results of Example 5, mesenchymal stem cells were divided into those which express CD26 and those which do not.

Specifically, the umbilical cord blood-derived mesenchymal stem cells were separated into a cell group which expresses CD26 (CD26+; positive cell group) and the other cell group which does not express CD26 (CD26−; negative cell group), using BD FACSAria™ III sorter device (BD Bioscience, Calif., USA). The mesenchymal stem cells of each group were treated with trypsin and washed once with PBS solution. The washed cells were reacted with each antigen CD26-PE. The signals of secondary antibodies were detected by BD FACSAria™ III sorter device, to assess the number of cells expressing a particular marker among the total cells. The regions where positive or negative cells are expressed at the level of 95% or higher were selected, and positive and negative groups were separately obtained using a device. The purity of each of the separated cell groups was assessed and only the cell group with 95% or higher purity was used in further experiments.

<7-2> Feature Analysis

Comparative analysis of the cell size, shape, proliferation capacity, and senescence capacity was conducted with regard to the above two cell groups separated in Example <7-1>(a cell group which expresses CD26 and the other cell group which does not).

(a) Comparison of morphological features

The size and shape of each cell were observed with a microscope.

Figure 16:
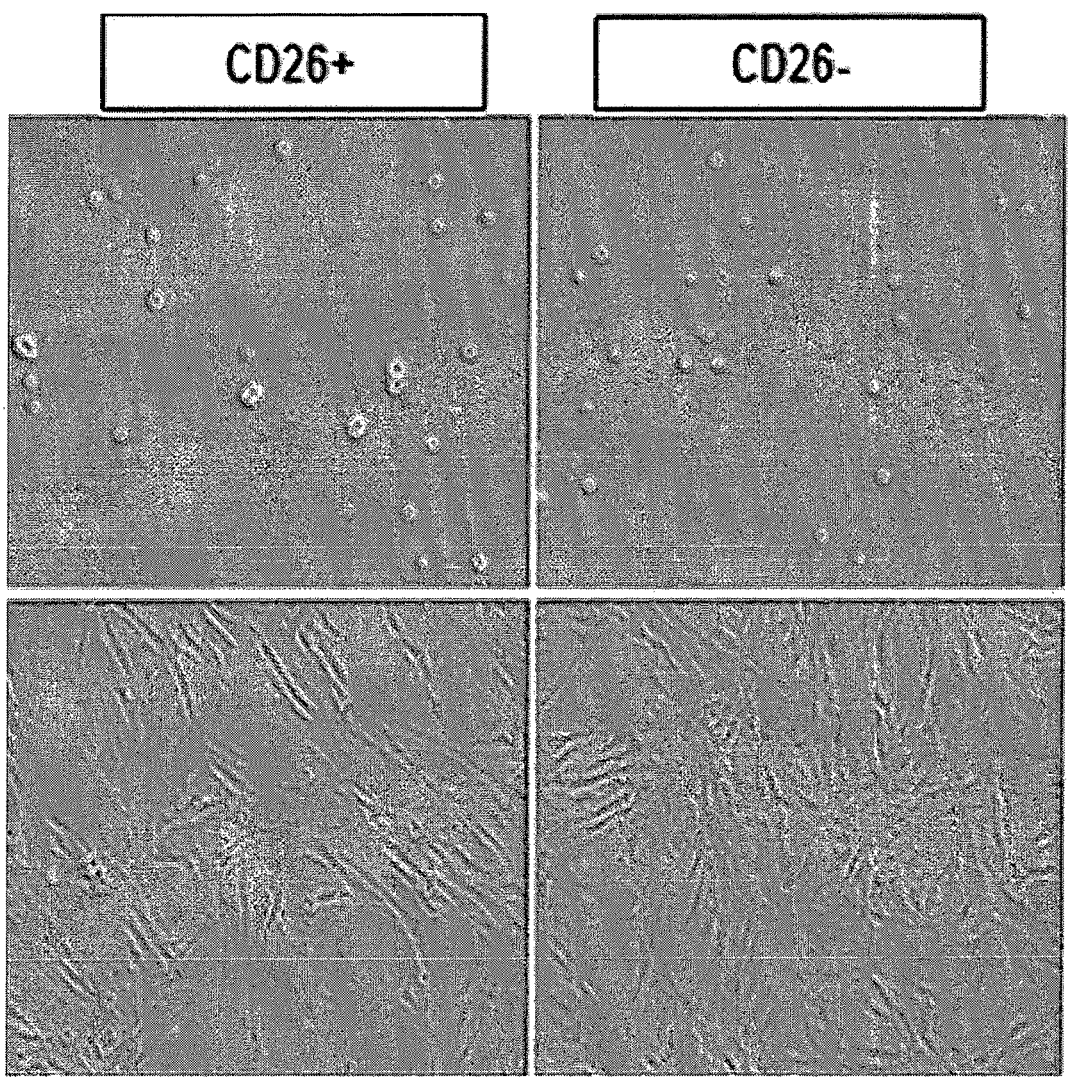
FIG. 16 provides microscopic photographs of the cells which express CD26 and those which do not, in a suspension state (upper part) and an adhesion state (lower part).

The results are shown in FIG. 16. FIG. 16 provides photographs showing the cells which express CD26 and those which do not, in a suspension state (upper part) and an adhesion state (lower part). As can be seen in FIG. 16, there could be found no remarkable differences in shape between the two groups, but the size of the cells which do not express CD26 was found to be smaller.

(b) Comparison of proliferation capacity

The mesenchymal stem cells at passage 5 were separated based on whether CD26 was expressed or not. And the proliferation capacity of each cell group was analyzed by the same method as Example <4-6>.

Figure 17:
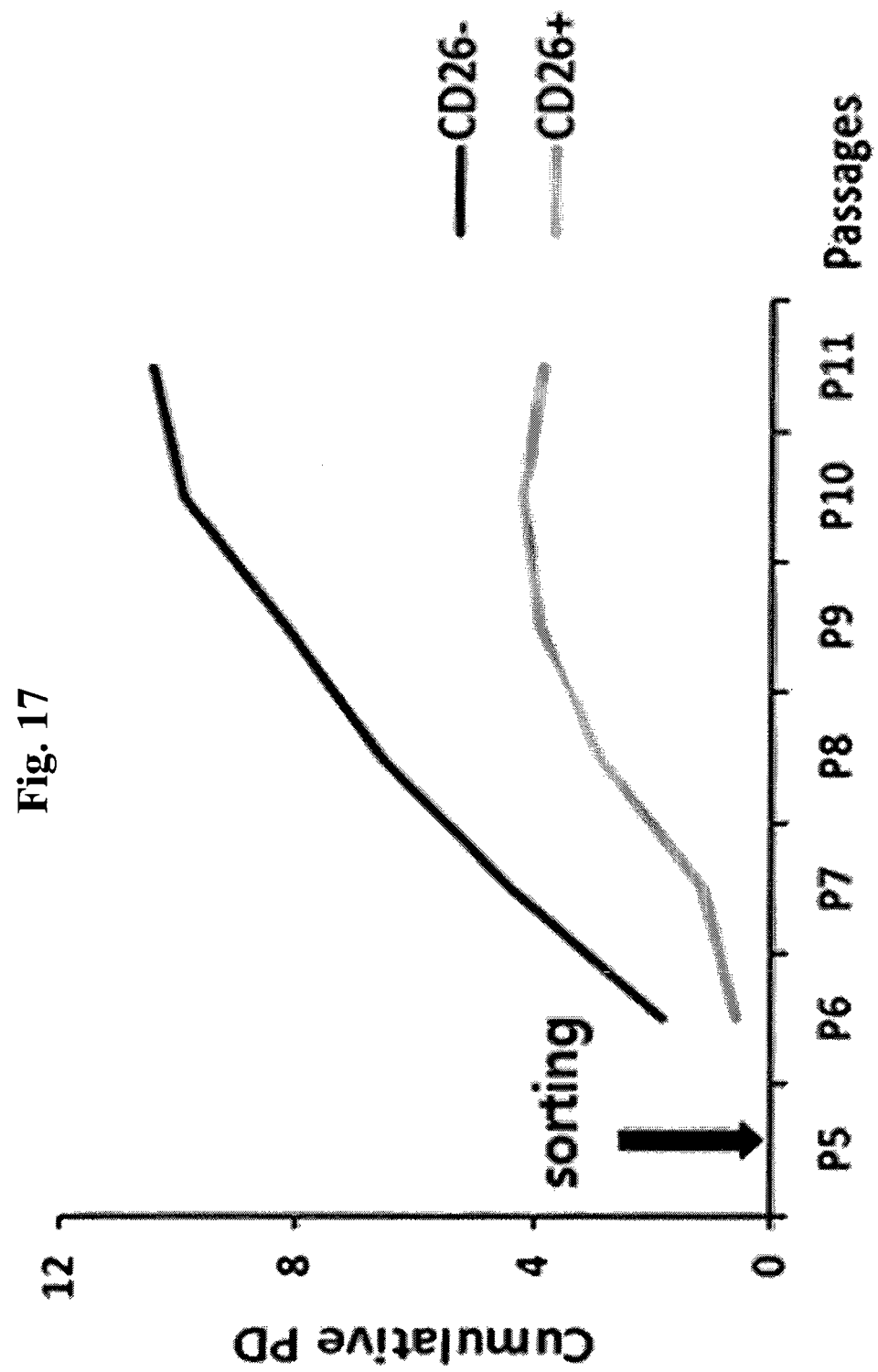
FIG. 17 is a graph showing CPD of the cells which express CD26 and those which do not.

The results are shown in FIG. 17. As can be seen in FIG. 17, the proliferation capacity of the cells which do not express CD26 was superior.

(c) Comparison of senescence

The senescence capacity of each cell group was analyzed by the same method as Example <4-7>.

Figure 18A:
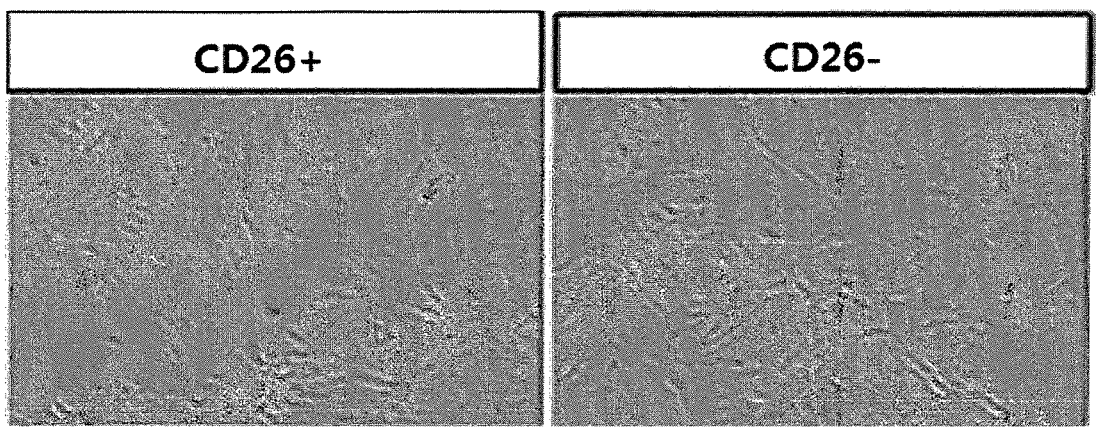
FIGS. 18A and 18B are photographs of the cells which express CD26 and those which do not, showing senescence-related staining (FIG. 18A), and the activity of senescence-related proteins examined by Western blot (FIG. 18B).
Figure 18B:
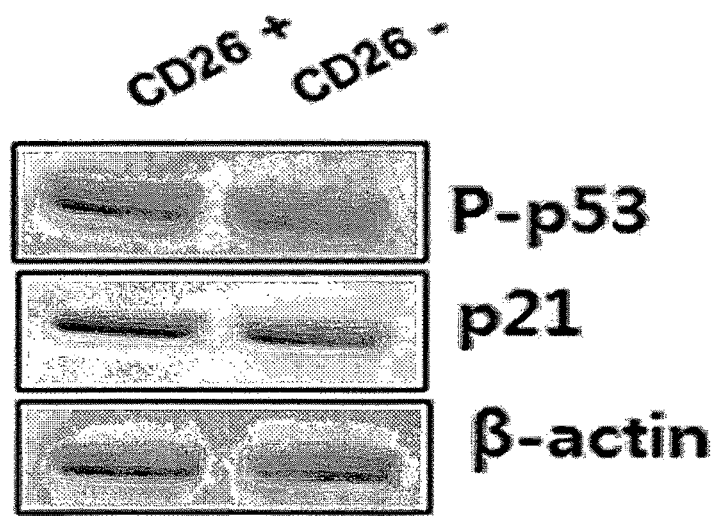

The results are shown in FIGS. 18A and 18B. FIGS. 18A and 18B are photographs showing the senescence-related staining in cells which express CD26 and those which do not (FIG. 18A), and the activity of senescence-related proteins examined by Western blot (FIG. 18B). As can be seen in FIGS. 18A and 18B, the expression levels of senescence-related proteins were lower in the cells which do not express CD26, indicating an excellent senescence inhibition capacity.

EXAMPLE 8

Cell Separation Depending on EGFR Expression and Feature Analysis

<8-1> Cell Separation Depending on EGFR Expression

Based on the results of Example 5, mesenchymal stem cells were divided into those which express EGFR and those which do not.

Specifically, the umbilical cord blood-derived mesenchymal stem cells were separated into a cell group which expresses EGFR (EGFR+; positive cell group) and the other cell group which does not express EGFR (EGFR−; negative cell group), using BD FACSAria™ III sorter device (BD Bioscience, Calif., USA). The mesenchymal stem cells of each group were treated with trypsin and washed once with PBS solution. The washed cells were reacted with each antigen EGFR-FITC. The signals of secondary antibodies were detected by BD FACSAria™ III sorter device, to assess the number of cells expressing a particular marker among the total cells. The regions where positive or negative cells are expressed at the level of 95% or higher were selected, and positive and negative groups were separately obtained using a device. The purity of each of the separated cell groups was assessed and only the cell group with 95% or higher purity was used in further experiments.

<8-2> Feature Analysis

Comparative analysis of the cell size, shape, osteogenic differentiation capacity, and senescence capacity was conducted with regard to the above two cell groups separated in Example <8-1>(a cell group which expresses EGFR and the other cell group which does not).

(a) Comparison of morphological features

The size and shape of each cell were observed with a microscope.

Figure 19:
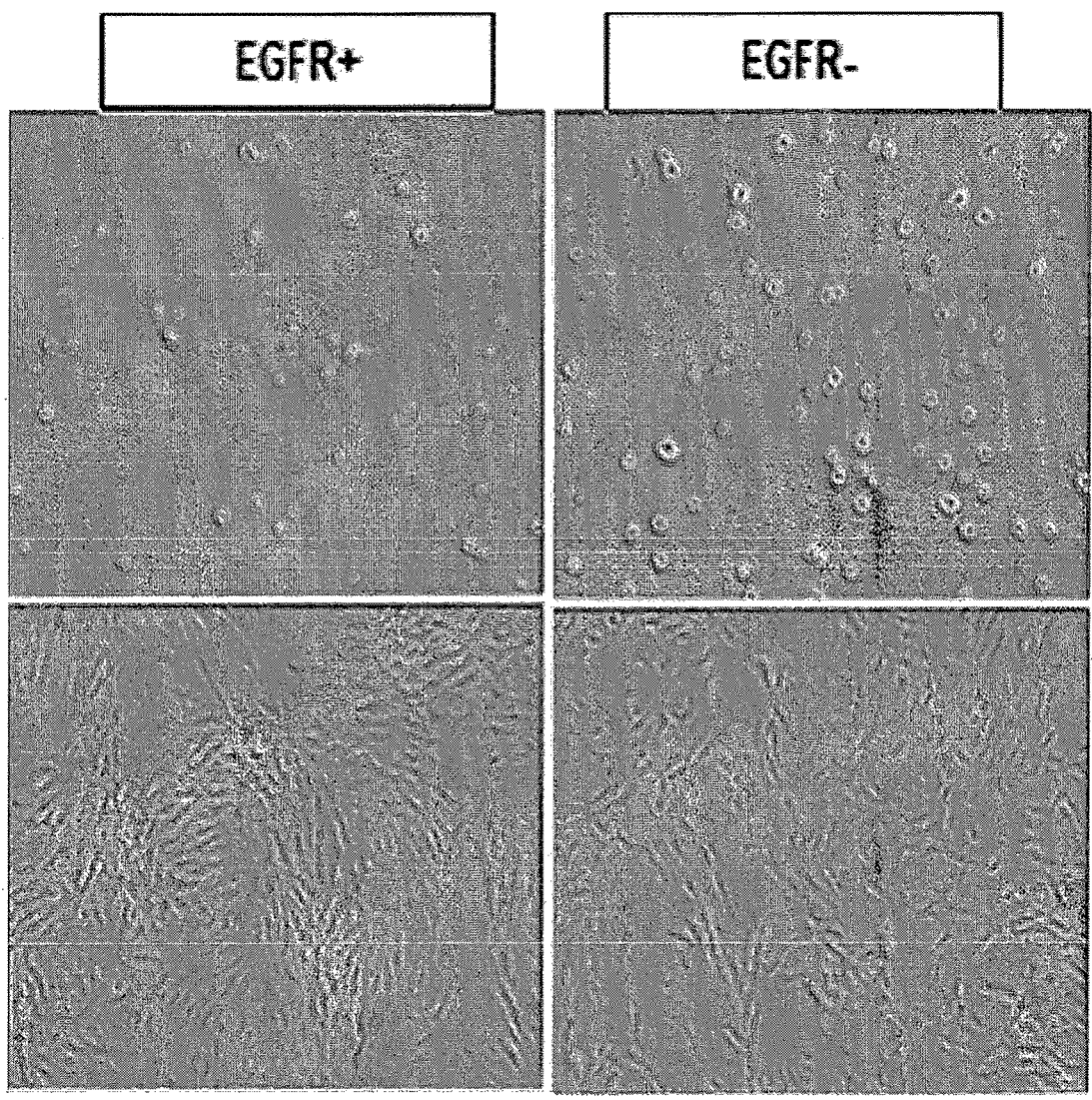
FIG. 19 provides microscopic photographs of the cells which express EGFR and those which do not, in a suspension state (upper part) and an adhesion state (lower part).

The results are shown in FIG. 19. FIG. 19 provides photographs showing the cells which express EGFR and those which do not, in a suspension state (upper part) and an adhesion state (lower part). As can be seen in FIG. 19, there could be found no remarkable differences in shape between the two groups, but the cell size was of the cells expressing EGFR was found to be smaller.

(b) Comparison of osteogenic differentiation capacity

The osteogenic differentiation capacity of each cell group was analyzed by the same method as Example <4-3>.

Figure 20:
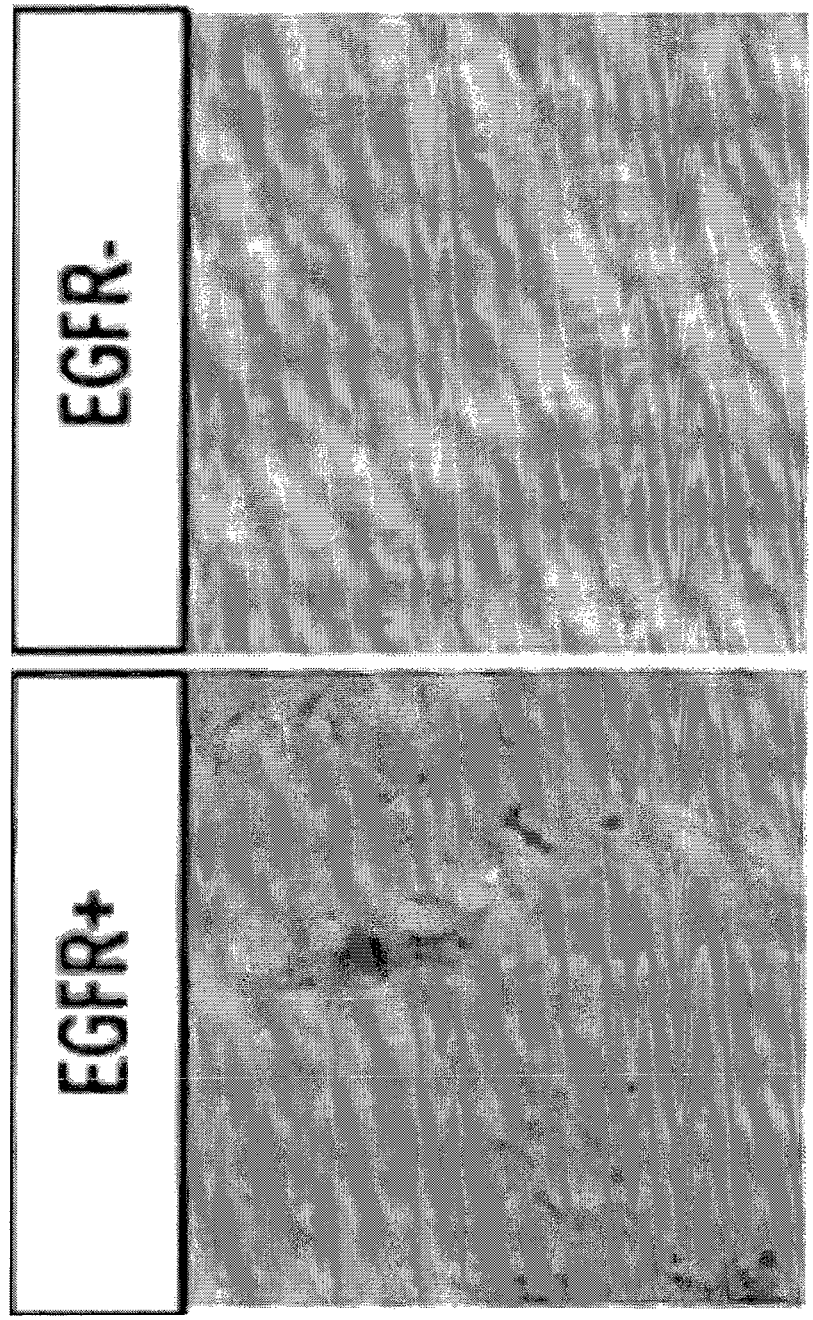
FIG. 20 provides photographs showing the osteogenic differentiation capacity of the cells which express EGFR and those which do not.

The results are shown in FIG. 20. As can be seen in FIG. 20, the osteogenic differentiation capacity of the cells expressing EGFR was superior.

(c) Comparison of senescence

The senescence capacity of each cell group was analyzed by the same method as Example <4-7>.

Figure 21A:
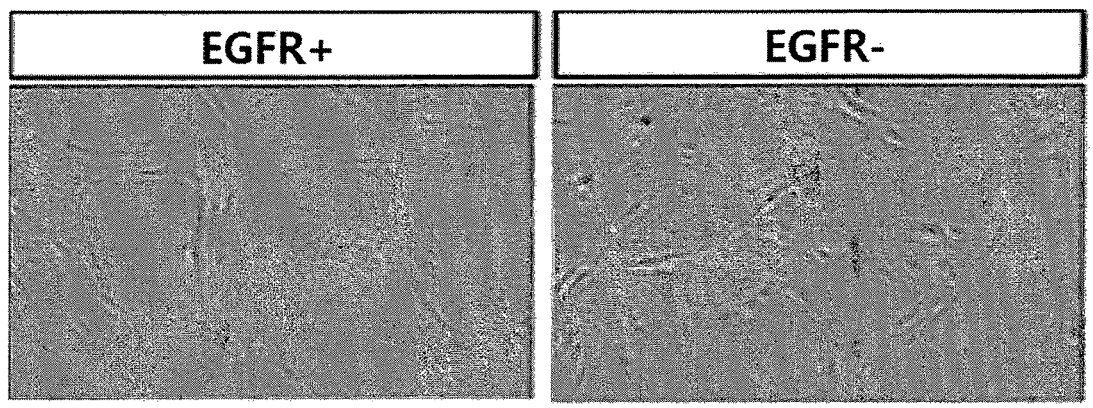
FIGS. 21A and 21B are photographs showing senescence-related staining (FIG. 21A) and the activity of senescence-related proteins examined by Western blot (FIG. 21B) of the cells which express EGFR and those which do not.
Figure 21B:
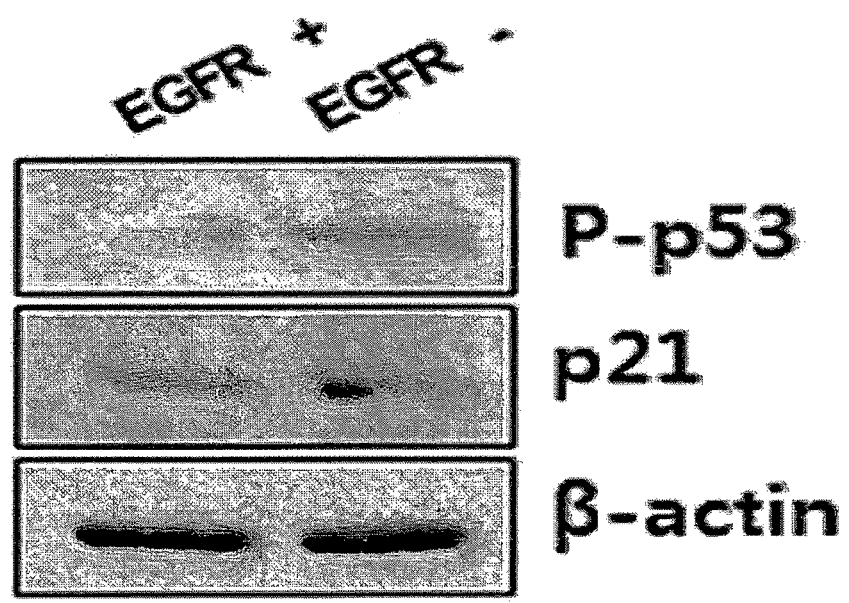

The results are shown in FIGS. 21A and 21B. FIGS. 21A and 21B are photographs showing the senescence-related staining in cells which express EGFR and those which do not (FIG. 21A), and the activity of senescence-related proteins examined by Western blot (FIG. 21B).

As can be seen in FIGS. 21A and 21B, the expression levels of senescence-related proteins were lower in the cells expressing EGFR, indicating an excellent senescence inhibition capacity.

EXAMPLE 9

Cell Separation Depending on CD49f Expression and Feature Aanalysis

<9-1> Cell Separation Depending on CD49f Expression

Based on the results of Example 5, mesenchymal stem cells were divided into those which express CD49f and those which do not.

Specifically, the umbilical cord blood-derived mesenchymal stem cells were separated into a cell group which expresses CD49f (CD49f+; positive cell group) and the other cell group which does not express CD49f (CD49f−; negative cell group), using BD FACSAria™ III sorter device (BD Bioscience, Calif., USA). The mesenchymal stem cells of each group were treated with trypsin and washed once with PBS solution. The washed cells were reacted with each antigen CD49f-Alex° 647. The signals of secondary antibodies were detected by BD FACSAria™ III sorter device, to assess the number of cells expressing a particular marker among the total cells. The regions where positive or negative cells are expressed at the level of 95% or higher were selected, and positive and negative groups were separately obtained using a device. The purity of each of the separated cell groups was assessed and only the cell group with 95% or higher purity was used in further experiments.

<9-2> Feature Analysis

Comparative analysis of the cell size, shape, osteogenic differentiation capacity, stem cell capacity and cell adhesion capacity was conducted with regard to the above two cell groups separated in Example <9-1>(a cell group which expresses CD49f and the other cell group which does not).

(a) Comparison of morphological features

The size and shape of each cell were observed with a microscope.

Figure 22:
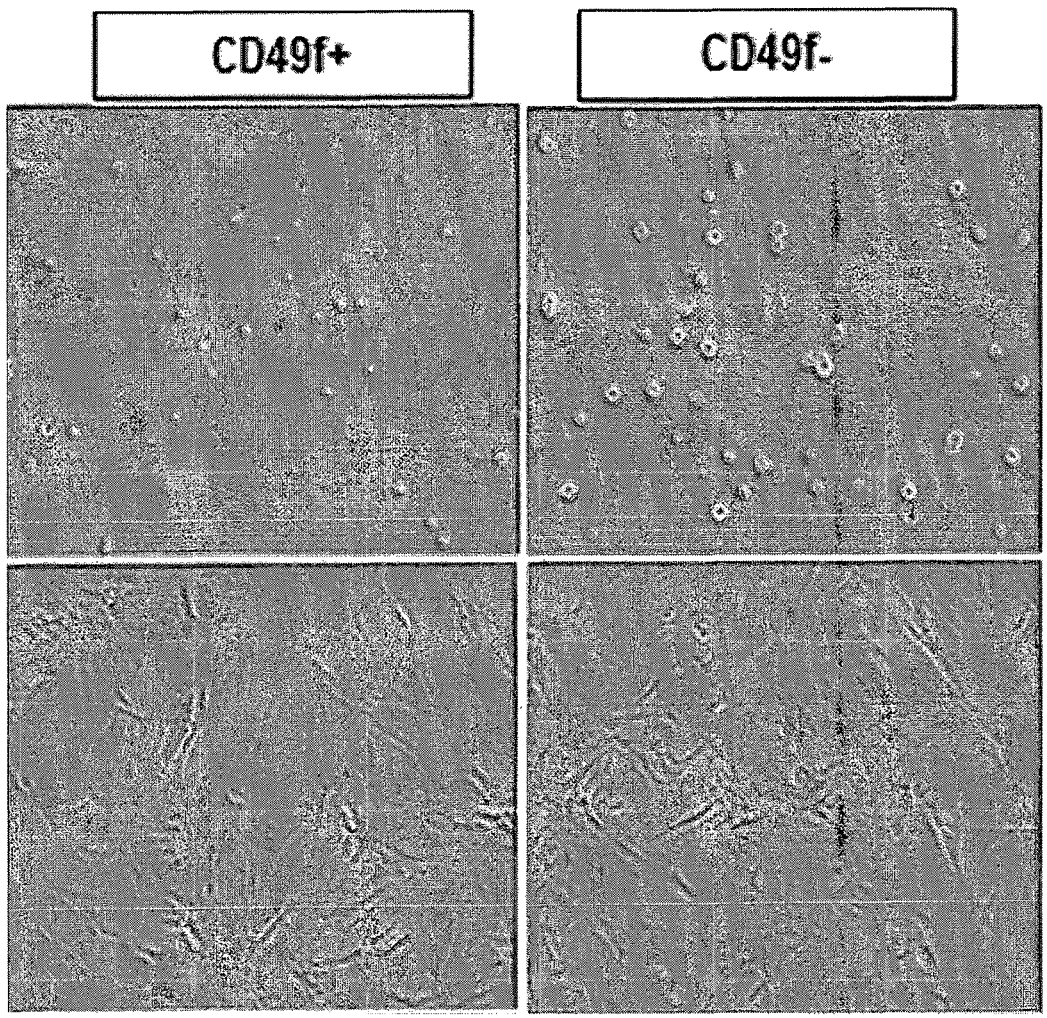
FIG. 22 provides photographs of the cells which express CD49f and those which do not, in a suspension state (upper part) and an adhesion state (lower part).

The results are shown in FIG. 22. FIG. 22 provides photographs showing the cells which express CD49f and those which do not, in a suspension state (upper part) and an adhesion state (lower part). As can be seen in FIG. 22, there could be found no remarkable differences in shape between the two groups, but the size of the cells expressing CD49f was found to be smaller.

(b) Comparison of osteogenic differentiation capacity

The osteogenic differentiation capacity of each cell group was analyzed by the same method as Example <4-3>.

Figure 23:
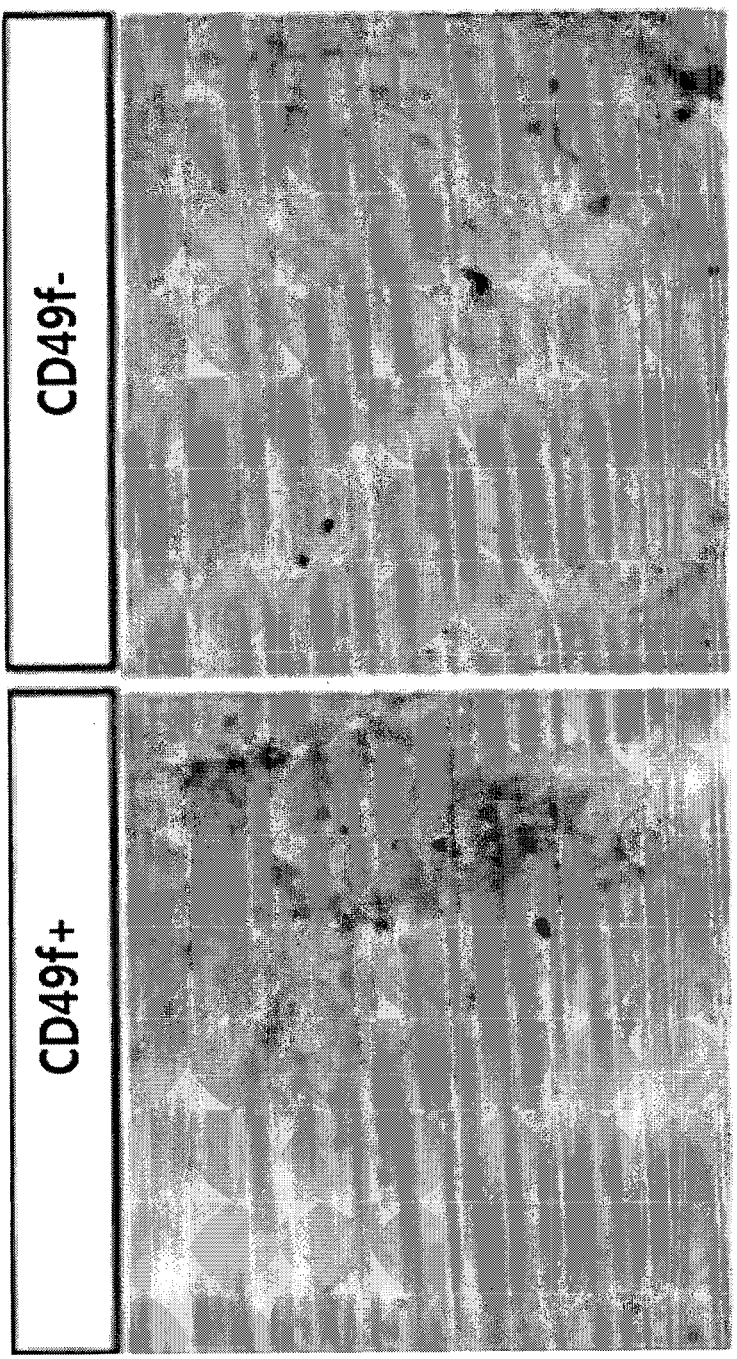
FIG. 23 provides photographs showing the osteogenic differentiation capacity of the cells which express CD49f and those which do not.

The results are shown in FIG. 23. As can be seen in FIG. 23, the osteogenic differentiation capacity of the cells expressing CD49f was superior.

(c) Comparison of stem cell capacity

The stem cell capacity of each cell group was analyzed by the same method as Example <4-8>.

Figure 24:
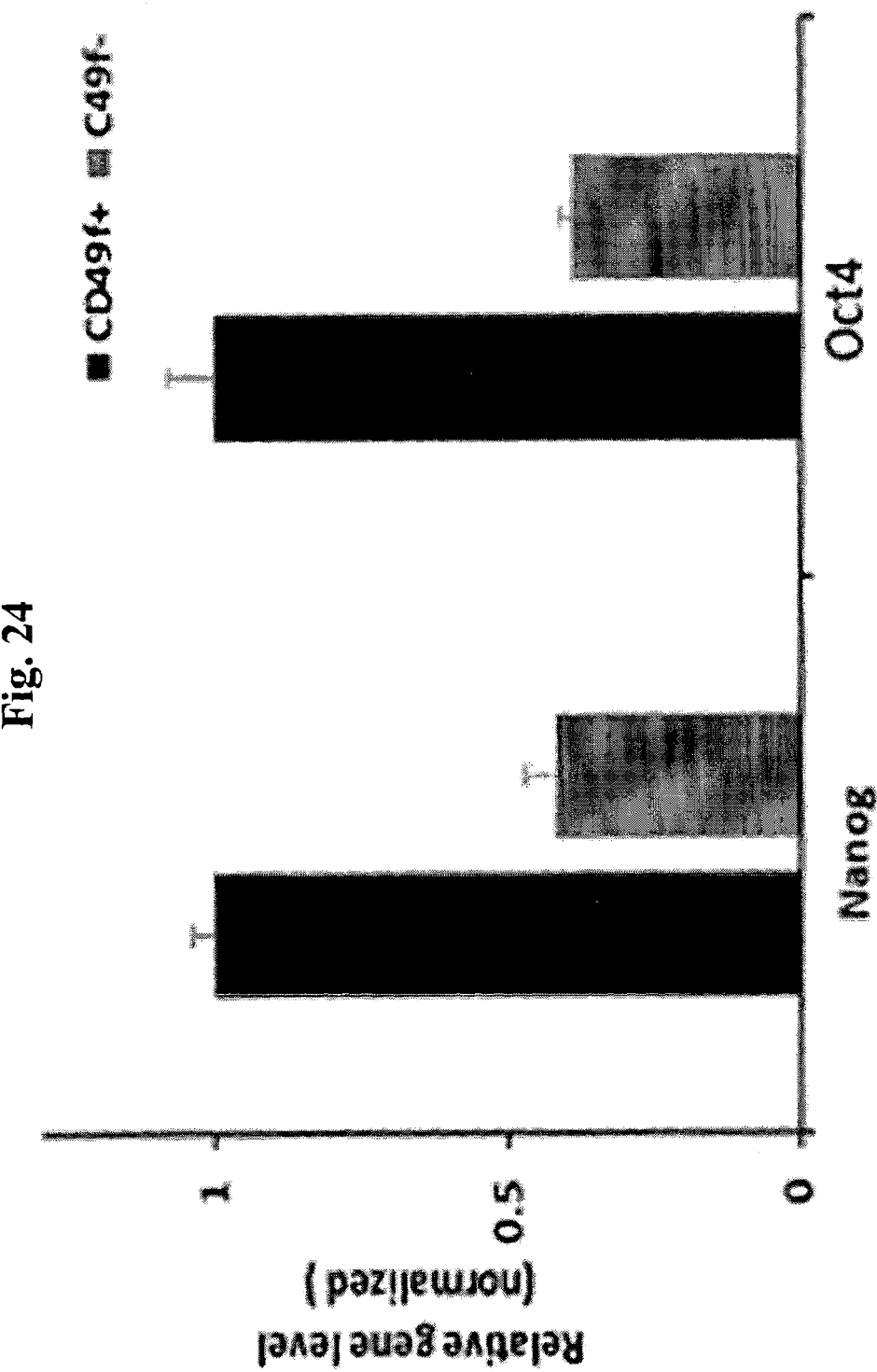
FIG. 24 provides a graph showing the stem cell capacity of the cells which express CD49f and those which do not.

The results are shown in FIG. 24. As can be seen in FIG. 24, the stem cell capacity of the cells expressing CD49f was superior.

(d) Comparison of cell adhesion capacity

The cell adhesion capacity of each cell group was analyzed by the same method as Example <4-9>.

Figure 25:
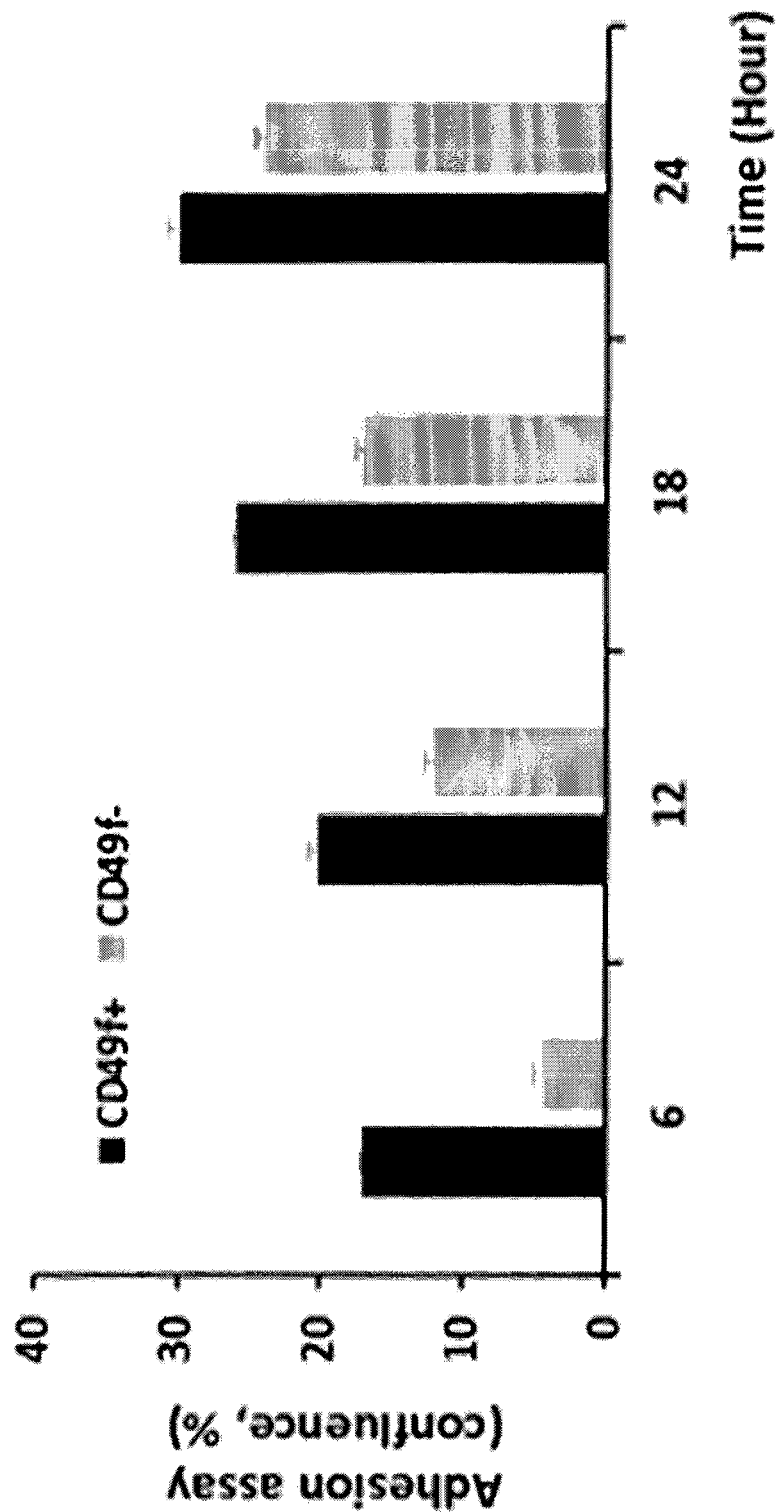
FIG. 25 provides a graph showing the adhesion capacity of the cells which express CD49f and those which do not.

The results are shown in FIG. 25. As can be seen in FIG. 25, the cell adhesion capacity of the cells expressing CD49f was superior.

EXAMPLE 10

Therapeutic Effect on Pulmonary Emphysema According to Cell Size

To examine the therapeutic effect of mesenchymal stem cells on a pulmonary disorder according to the cell size, two cell groups were prepared. One group contained cells having a size of 8 μm or less in a ratio of 8% (Group 1; G1), and the other group contained cells having a size of 8 μm or less in a ratio of 40% (Group 2; G2).

<10-1> Establishment of a Model Mouse of Pulmonary Emphysema

Meanwhile, 6-week-old C57BL/6 mice were domesticated in an animal room for one week, and then anesthetized by intra-peritoneal injection of an anesthetic solution in which Zoletil 50 (Virbac, Carros, France) and Rompun (Bayer, Leverkusen, Germany) were diluted to 1/10 in Dulbecco's phosphate-buffered saline (D-PBS Biowest, NUAILLE FRANCE) with their mixing ratio of 4:1. The anesthetized mice received intra-tracheal administration of 0.4 U of porcine pancreas in the form of elastase (Sigma-Aldrich, St. Louis, Mo., USA) using Gel-Saver II tips (USA Scientific, Ocala, Fla., USA), at 50 μl per mouse, to establish the pulmonary emphysema model.

<10-2> Administration of Mesenchymal Stem Cells

Then, the umbilical cord blood-derived mesenchymal stem cells suitable for each condition were injected into the tail vein of each mouse by using BD Ultra-Fine Insulin syringe (BD, Franklin Lake, N.J., USA) at $2\times10^4$ cells/D-PBS 100 μl. One week after the cell administration, the lung of each mouse was extracted, and 0.5% agarose (low gelling temperature; Sigma-Aldrich, St. Louis, Mo., USA) was inserted into the bronchus, which was then fixated using 4% para-formaldehyde (Sigma-Aldrich, St. Louis, Mo., USA) for 24 hours. After completion of the fixation process, paraffin blocks were produced, cut into slides of 5 μm thickness, and then subjected to H & E and various kinds of stainings.

<10-3> Analysis of Alveolar Size by H & E Stain

For H & E staining, the slides were reacted with Hematoxylin for 1 minute, washed, and then reacted with Eosin for 30 seconds. Then, the dyes were appropriately removed in 70% ethanol, and then the stained areas were observed by an optical microscope (ChemiDoc™ MP Imsenescence System; Bio-Rad, Hercules, Calif., USA).

Also, in order to determine the amount of lung tissue damage, the MLI (Mean linear intercept) analysis was conducted. Specifically, the H & E stained slides of each group were examined by using a tissue microscope (100×), to measure the average inter-alveolar wall distance. In a randomly selected field of view which does not contain blood vessels or trachea, the points included in a 1000 μm long reference line was counted. Then, the length of the reference line (1000 μm) was divided by the number of points counted, to obtain the inter-alveolar wall distance, which was set as the mean linear intercept. Five or more fields of view were examined per slide, and the mean value of the counted values was obtained.

Figure 26:
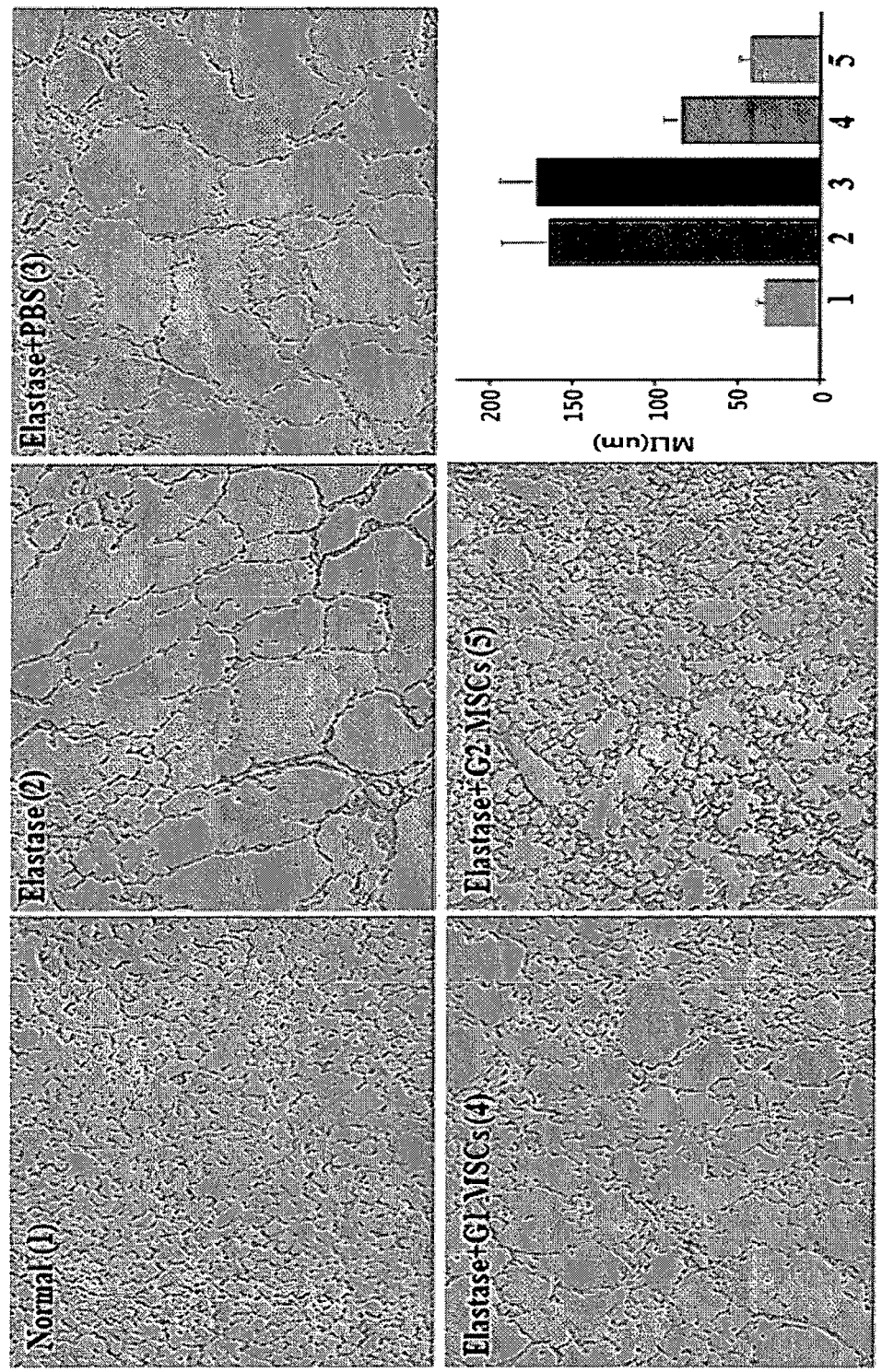
FIG. 26 provides photographs showing H & E staining of the alveoli in the groups of: (1) normal cells; (2) cells treated with elastase; (3) cells treated with elastase and PBS; (4) cells treated with elastase and stem cells G1; and (4) cells treated with elastase and stem cells G2.

The H & E stain and MLI measurement results are shown in FIG. 26.

As can be seen in FIG. 26, the size of the alveoli damaged by elastase was decreased by the administration of mesenchymal stem cells G1 and G2. Specifically, the size of the alveoli showed significantly greater decrease with G2 (which contained a large amount of small cells) as compared to G1 (which contained a small amount of is small cells).

<10-4> Analysis of Lung Vessels by vWF Fluorescence Staining

To determine the differences between the endothelial cells of the lung tissue according to the administration of umbilical cord blood-derived mesenchymal stem cells, the slides of each group were stained with vWF (von Willebrand Factor) antibody. More particularly, only the tissue part on the slide was selected and marked. Then, the tissue was fixated by peroxidase blocking solution (DAKO, Produktionsvej, Denmark), washed, and then reacted with vWF primary antibody (Millipore, Temecula, Calif., USA) at room temperature for 1 hour. The tissue was washed, and then reacted with a secondary antibody anti-rabbit IgG FITC (Jackson Immunoresearch, West Grove, Pa., USA) at room temperature in a light shielded state for 1 hour. The tissue was washed, and then stained with Hoechet 3342 (Invitrogen Molecular Probes, Eugene, Oreg., USA) at room temperature for 5 minutes for nuclear staining The stained slides were observed using a fluorescence microscope.

The staining value of each group was quantitatively analyzed as compared to normal group which was set at 100% of staining value. The vWF fluorescence staining results are shown in FIG. 27.

Figure 27:
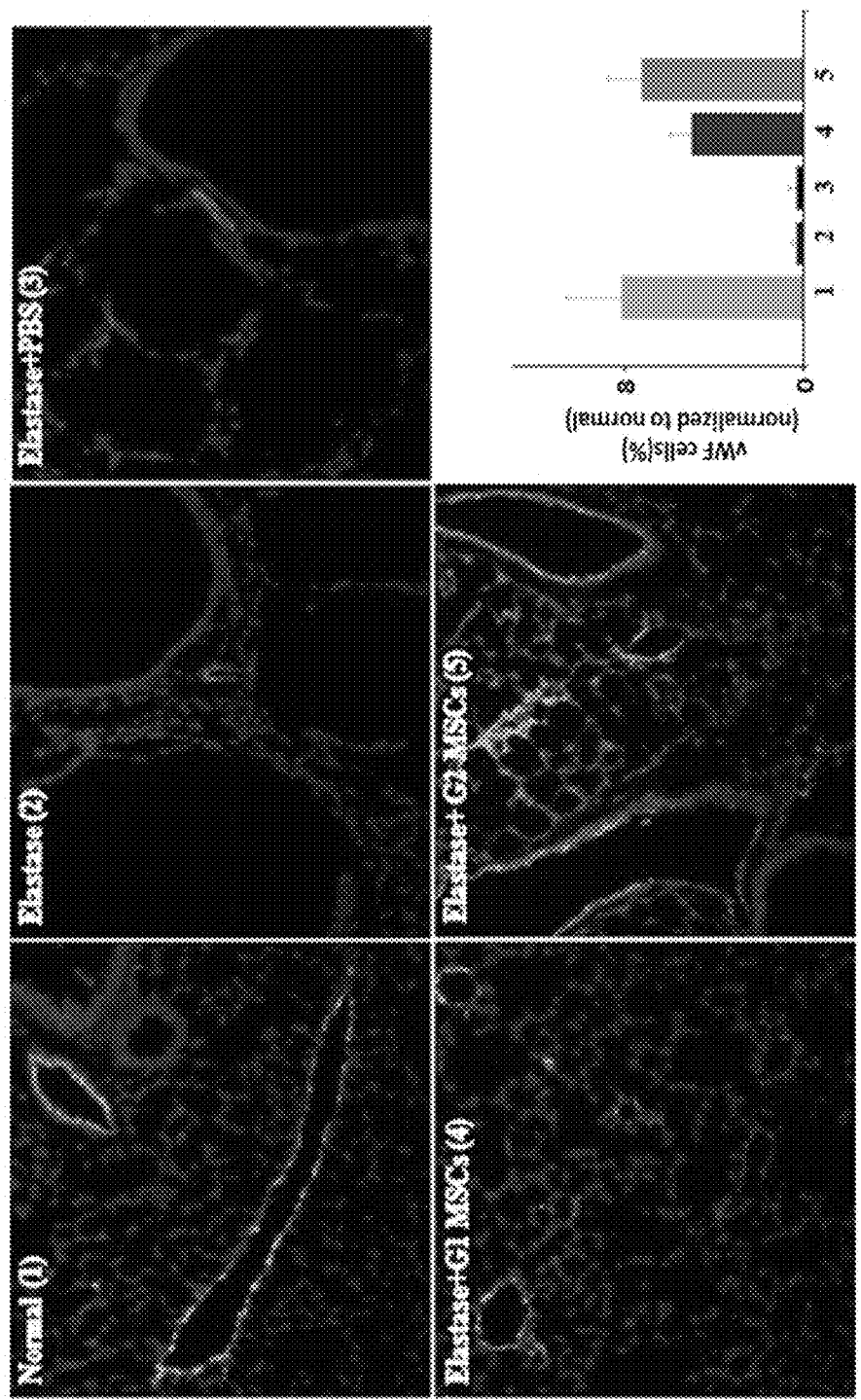
FIG. 27 provides photographs showing vWF fluorescence staining and a graph showing the staining values, in the groups of: (1) normal cells; (2) cells treated with elastase; (3) cells treated with elastase and PBS; (4) cells treated with elastase and stem cells G1; and (4) cells treated with elastase and stem cells G2.

As can be seen in FIG. 27, the lung vessels damaged by elastase were shown to have recovered by the administration of mesenchymal stem cells G1 or G2. Specifically, G2 which contained a large amount of small cells showed higher efficacy as compared to G1 which contained a small amount of small cells.

EXAMPLE 11

Therapeutic Effect of Mesenchymal Stem Cells Having a Size of 8 μm or Less on Pulmonary Emphysema Therapeutic effect on pulmonary emphysema were examined using the cells having a size of 8 μm or less separated in the Example <3-2>and the cells before size separation, in the same manner as in Example 10.

is <11-1> Analysis of Alveolar Size by H & E Stain

H & E staining and MLI analysis were conducted in the same manner as in Example <10-3>. The experimental result is shown in FIG. 28.

Figure 28:
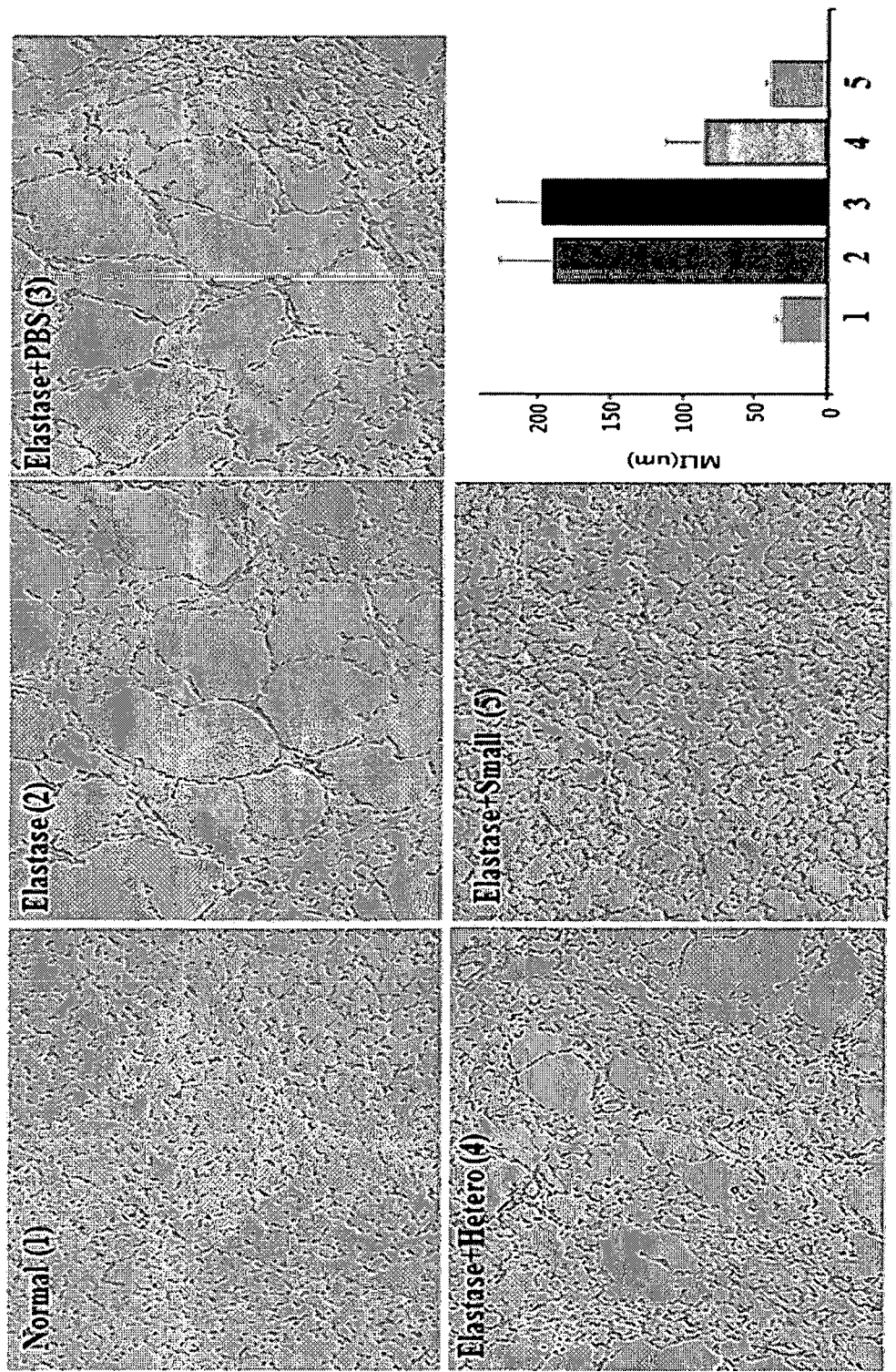
FIG. 28 provides photographs showing H & E staining of the alveoli and a graph showing the MLI in the groups of: (1) normal cells; (2) cells treated with elastase; (3) cells treated with elastase and PBS; (4) cells treated with elastase and stem cells before size separation; and (5) cells treated with elastase and stem cells after size separation.

As can be seen in FIG. 28, the size of the alveoli damaged by elastase was decreased by the administration of mesenchymal stem cells before size separation or mesenchymal stem cells having a size of 8 μm or less. Specifically, the mesenchymal stem cells having a size of 8 μm or less showed higher efficacy as compared to the mesenchymal stem cells before size separation.

<11-2> Analysis of Lung Vessels by vWF Fluorescence Staining

The vWF fluorescence staining was conducted in the same manner as in Example <10-4>. The staining value of each group was analyzed as compared to normal group which was set at 100% of staining value. The results are shown in FIG. 29.

Figure 29:
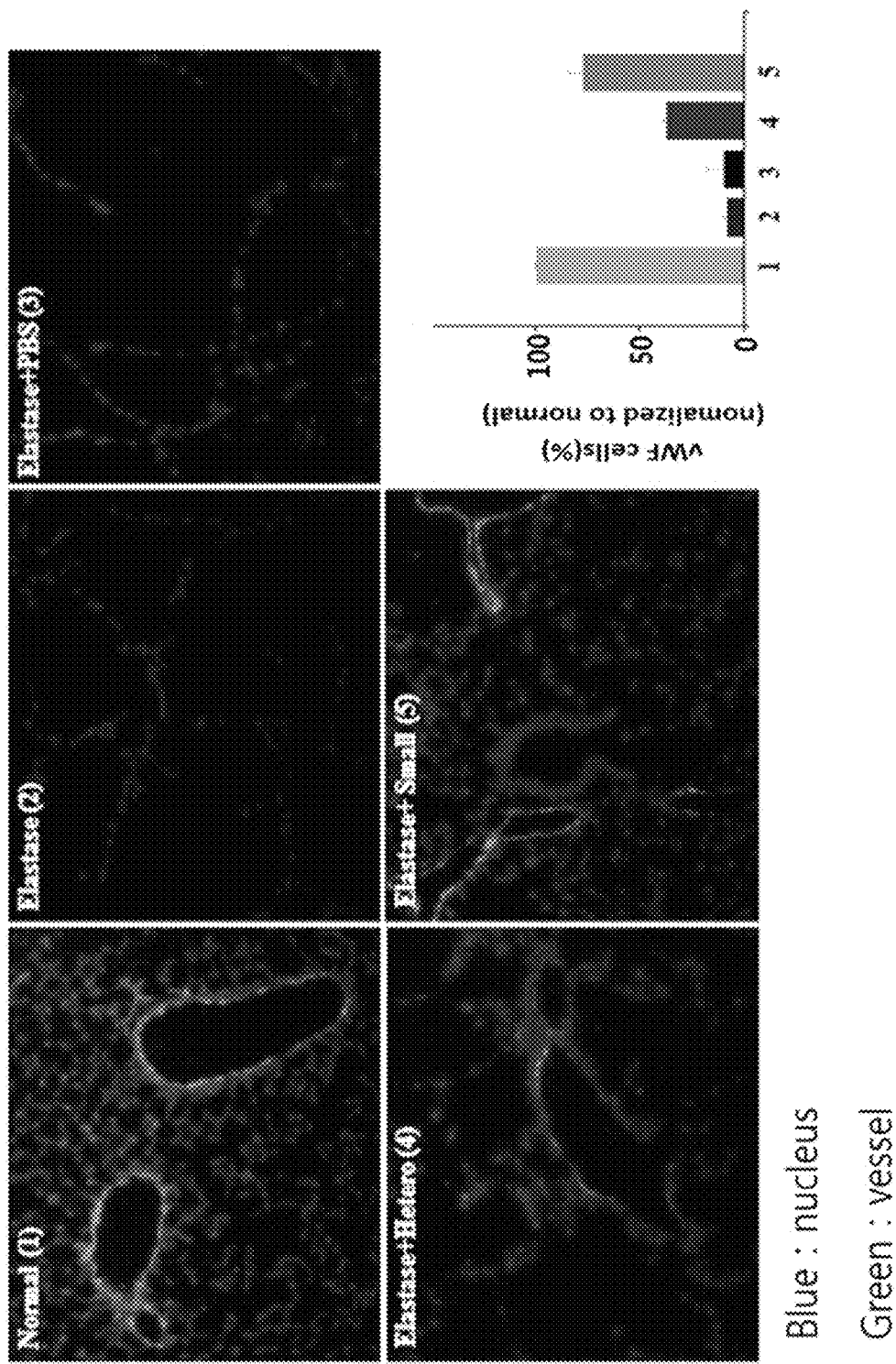
FIG. 29 provides photographs showing vWF fluorescence staining and a graph showing the staining values, in the groups of: (1) normal cells; (2) cells treated with elastase; (3) cells treated with elastase and PBS; (4) cells treated with elastase and stem cells before size separation; and (5) cells treated with elastase and stem cells after size separation.

As can be seen in FIG. 29, the lung vessels damaged by elastase were shown to have recovered by the administration of mesenchymal stem cells before size separation or mesenchymal stem cells having a size of 8 μm or less. Specifically, the mesenchymal stem cells having a size of 8 μm or less showed higher efficacy.

EXAMPLE 12

Analysis of Remaining Implanted Human-Derived Mesenchymal Stem Cells by β2MG Fluorescence Staining To identify the remaining umbilical cord blood-derived mesenchymal stem cells in the lung tissue after administration of the mesenchymal stem cells, slides of two groups were prepared (one group of cells having a size of 8 μm or less and the other group of cells before size separation). Then the cells were stained with β2MG (β2 microglobulin) antibody in the same manner as Example <10-2>.

More particularly, to examine the cells before and after size separation, only the tissue part on the slide was selected and marked. Then, the tissue was fixated by peroxidase blocking solution (DAKO, Produktionsvej, Denmark), washed, and then is reacted with β2MG primary antibody (Abcam, Cambridge, Mass., USA) at room temperature for 1 hour. The tissue was washed, and then reacted with a secondary antibody anti-rabbit IgG FITC (Jackson Immunoresearch, West Grove, Pa., USA) at room temperature in a light shielded state for 1 hour. The tissue was washed, and then stained with Hoechet 3342 (Invitrogen Molecular Probes, Eugene, Oreg., USA) at room temperature for 5 minutes, for nuclear staining The stained slides were observed using a fluorescence microscope.

Figure 30A:
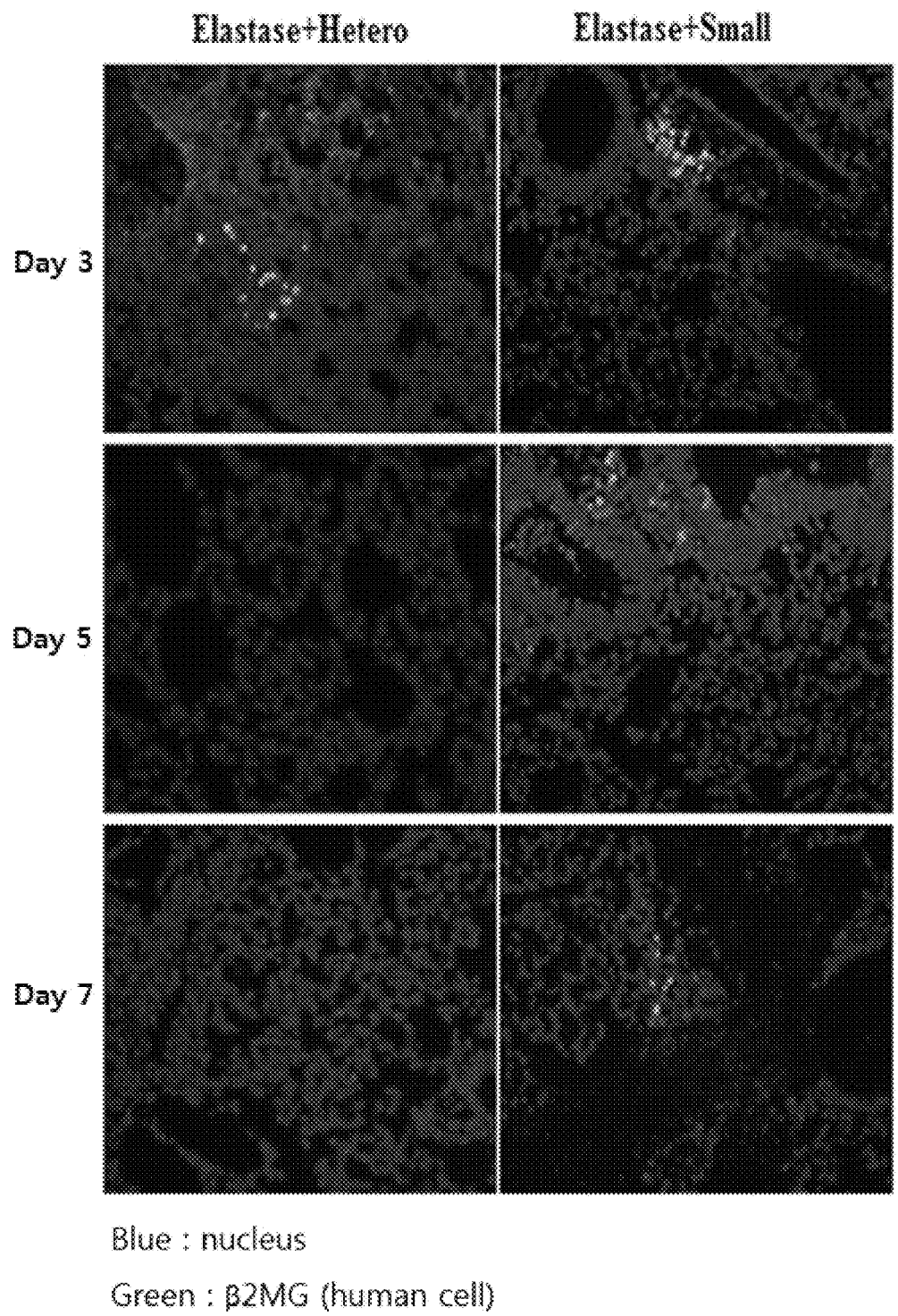
FIGS. 30A and 30B provide photographs (FIG. 30A) and a graph (FIG. 30B) showing the staining of the cells with β2MG at different time points, to determine whether the mesenchymal stem cells before and after size separation remained in lung tissues.
Figure 30B:
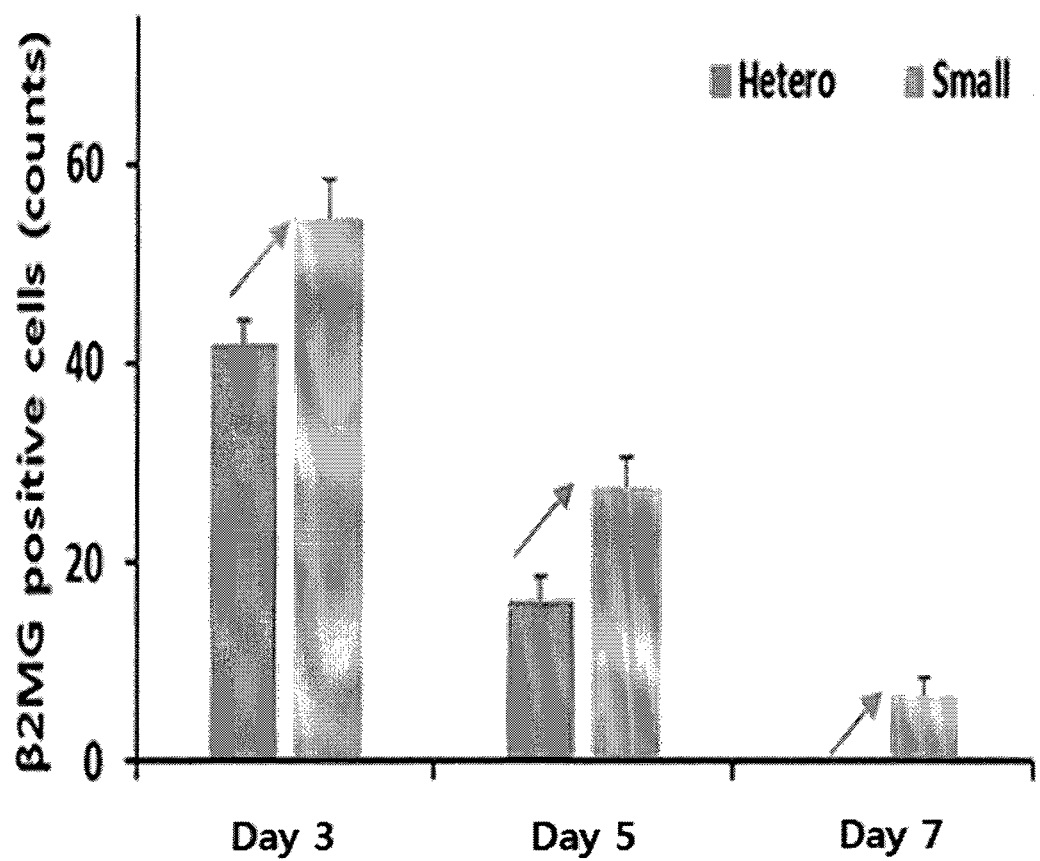

The β2MG fluorescent staining results are shown in FIGS. 30A and 30B. In each experimental group, the cells stained with β2MG were counted for analysis. The group without administration of the umbilical cord blood-derived mesenchymal stem cells did not show staining with β2MG.

As can be seen in FIGS. 30A and 30B, upon examination of the remaining cells 3, 5 and 7 days after their administraion, the mesenchymal stem cells having a size of 8 μm or less were shown to have remained in the lung tissue for longer period than the mesenchymal stem cells before size separation. Specifically, 7 days after the administration, only the mesenchymal stem cells having a size of 8 μm or less were observed to have remained. These results indicate that the survival rate of the mesenchymal stem cells having a size of 8 μm or less is higher than mesenchymal stem cells before size separation.

The invention claimed is:

1. A method for preventing and/or treating a pulmonary disorder in a subject in need thereof, comprising administering a composition comprising mesenchymal stem cells as an active ingredient to the subject,
wherein the mesenchymal stem cells do not express cluster of differentiation (CD) 26 as a cell marker, and
wherein the mesenchymal stem cells have a size of 8 μm or less.

2. The method of claim 1, wherein the mesenchymal stem cells express at least one of CD49f, CD146, and epidermal growth factor receptor (EGFR) as a cell marker.

3. The method of claim 1, wherein the mesenchymal stem cells express CD49f, CD146, and EGFR.

4. The method of claim 3, wherein the mesenchymal stem cells express CD49f, CD146, and EGFR to levels which are higher by more than 50%, more than 90%, and more than 50%, respectively, as compared to mesenchymal stem cells expressing CD26.

5. The method of claim 1, wherein the mesenchymal stem cells are derived from umbilical cord blood, bone marrow, lipid, muscle, skin, amniotic fluid, umbilical cord or tooth.

6. The method of claim 1, wherein mesenchymal stem cells are obtained by
bringing a solution containing mesenchymal stem cells to be in contact with an agent which specifically binds to the CD26 to separate mesenchymal stem cells expressing CD26 from those not expressing CD26;
bringing a solution containing mesenchymal stem cells to be in contact with one or more of agents which each specifically bind to one of CD49f, CD146, and EGFR to separate mesenchymal stem cells expressing at least one of CD49f, CD146, and EGFR from those not expressing any of CD49f, CD146, and EGFR; and
subjecting the solution containing mesenchymal stem cells to a size separation to separate mesenchymal stem cells of 8 μm or less in size.

7. The method of claim 6, wherein the agent which specifically binds to the CD26 is a CD26 antigen, and the one or more agents which each specifically bind to one of CD49f, CD146, and EGFR are one or more of CD49f antigen, CD146 antigen, and EGFR antigen.

8. The method of claim 1, wherein the pulmonary disorder is damaged lung tissue.

9. A method for regenerating pulmonary cells in a subject in need thereof, comprising administering a composition comprising mesenchymal stem cells as an active ingredient to the subject, wherein the mesenchymal stem cells do not express cluster of differentiation 26 (CD26) as a cell marker, and
wherein the size of the mesenchymal stem cells is 8 μm or less.

10. The method of claim 9, wherein the mesenchymal stem cells express at least one selected from cluster of differentiation 49f (CD49f), cluster of differentiation 146 (CD146) and epidermal growth factor receptor (EGFR) as a cell marker.

11. The method of claim 9, wherein the mesenchymal stem cells express CD49f, CD146, and EGFR as cell markers.

12. The method of claim 11, wherein the mesenchymal stem cells express CD49f, CD146, and EGFR to levels which are higher by more than 50%, more than 90%, and more than 50%, respectively, as compared to mesenchymal stem cells expressing CD26.

13. The method of claim 9, wherein the mesenchymal stem cells are derived from umbilical cord blood, bone marrow, lipid, muscle, skin, amniotic fluid, umbilical cord or tooth.

14. The method of claim 9, wherein mesenchymal stem cells are obtained by
bringing a solution containing mesenchymal stem cells to be in contact with an agent which specifically binds to the CD26 to separate mesenchymal stem cells expressing CD26 from those not expressing CD26;
bringing a solution containing mesenchymal stem cells to be in contact with one or more of agents which each specifically bind to one of CD49f, CD146, and EGFR to separate mesenchymal stem cells expressing at least one of CD49f, CD146, and EGFR from those not expressing any of CD49f, CD146, and EGFR; and
subjecting the solution containing mesenchymal stem cells to a size separation to separate mesenchymal stem cells of 8 μm or less in size.

15. The method of claim 14, wherein the agent which specifically binds to the CD26 is a CD26 antigen, and the one or more agents which each specifically bind to one of CD49f, CD146, and EGFR are one or more of CD49f antigen, CD146 antigen, and EGFR antigen.

* * * * *